(12) United States Patent
Hagstrom et al.

(10) Patent No.: US 7,803,782 B2
(45) Date of Patent: Sep. 28, 2010

(54) INTRAVENOUS DELIVERY OF POLYNUCLEOTIDES TO CELLS IN MAMMALIAN LIMB

(75) Inventors: James E. Hagstrom, Middleton, WI (US); Julia Hegge, Monona, WI (US); Hans Herweijer, Brooklyn, WI (US); Jon A. Wolff, Madison, WI (US)

(73) Assignee: Roche Madison Inc., Madison, WI (US)

( * ) Notice: Subject to any disclaimer, the term of this patent is extended or adjusted under 35 U.S.C. 154(b) by 296 days.

(21) Appl. No.: 10/855,175

(22) Filed: May 27, 2004

(65) Prior Publication Data

US 2004/0242528 A1  Dec. 2, 2004

Related U.S. Application Data

(60) Provisional application No. 60/473,654, filed on May 28, 2003, provisional application No. 60/500,211, filed on Sep. 4, 2003.

(51) Int. Cl.
*A61K 48/00* (2006.01)
*A61M 31/00* (2006.01)

(52) U.S. Cl. .................................. 514/44; 604/500

(58) Field of Classification Search ................ 435/69.1, 435/320.1, 325, 455; 424/93.1; 514/44
See application file for complete search history.

(56) References Cited

U.S. PATENT DOCUMENTS

| | | | |
|---|---|---|---|
| 5,521,291 A | 5/1996 | Curiel et al. | |
| 5,580,859 A | 12/1996 | Felgner et al. | |
| 5,583,020 A | 12/1996 | Sullivan | |
| 5,698,531 A | 12/1997 | Nabel et al. | |
| 5,744,335 A | 4/1998 | Wolff et al. | |
| 5,922,687 A | 7/1999 | Mann et al. | |
| 6,177,403 B1 * | 1/2001 | Stedman | 514/2 |
| 6,265,387 B1 * | 7/2001 | Wolff et al. | 514/44 |
| 6,495,131 B1 | 12/2002 | Draijer-van der Kaaden | |
| 6,627,616 B2 | 9/2003 | Monahan et al. | |
| 6,699,231 B1 * | 3/2004 | Sterman et al. | 604/509 |
| 2004/0136960 A1 | 7/2004 | Wolff et al. | |
| 2004/0224879 A1 | 11/2004 | Wolff et al. | |

FOREIGN PATENT DOCUMENTS

WO          WO0113723        5/2001

OTHER PUBLICATIONS

Liu et al (J. Bio. Chem 270(42):24864-24870, 1995.*
Acsadi G et al. "Direct gene transfer and expression into rat heart in vivo," The New Biologist; 1991 vol. 3, No. 1 pp. 71-81.
Baumgartner I et al. "Stimulation of peripheral angiogenesis by vascular endothelial growth factor (VEGF)." Vasa. 1998 vol. 27 No. 4 pp. 201-206.
Blau HM et al. "Muscle-mediated gene therapy." N Engl J Med. 1995 vol. 333 No. 23 pp. 1554-1556.
Budker V et al. "Naked DNA delivered intraportally expresses efficiently in hepatocytes." Gene Therapy; 1996 vol. 3 No. 7 pp. 593-598.
Budker V et al. "The efficient expression of intravascularly delivered DNA in rat muscle," Gene Therapy; 1998 vol. 5 No. 2 pp. 272-276.
DelloRusso C et al. "Functional correction of adult mdx mouse muscle using gutted adenoviral vectors expressing full-length dystrophin." Proc Natl Acad Sci USA, 2002 vol. 99 No. 20 pp. 12979-12984.
Eastman SJ et al. "Development of catheter-based procedures for transducing the isolated rabbit liver with plasmid DNA." Hum Gene Ther. 2002 vol. 13 No. 17 pp. 2065-2077.
Elbashir SM et al. "Duplexes of 21-nucleotide RNAs mediate RNA interference in cultured mammalian cells." Nature. 2001 vol. 411 No. 6836 pp. 494-498.
Fabb SA et al. "Adeno-associated virus vector gene transfer and sarcolemmal expression of a 144 kDa micro-dystrophin effectively restores the dystrophin-associated protein complex and inhibits myofibre degeneration in nude/mdx mice." Hum Mol Genet 2002 vol. 11 No. 7 pp. 733-741.
Goldspink G et al. "Skeletal muscle as an artificial endocrine tissue." Best Pract Res Clin Endocrinol Metab. 2003 vol. 17 No. 2 pp. 211-222.
Greelish JP et al. "Stable restoration of the sarcoglycan complex in dystrophic muscle perfused with histamine and a recombinant adeno-associated viral vector." Nature; 1999 vol. 5 No. 4 pp. 439-443.
Gregorevic P et al. "Gene therapy for muscular dystrophy—a review of promising progress." Expert Opin Biol Ther 2003 vol. 3 No. 5 pp. 803-814.
Hengge UR et al. "Cytokine gene expression in epidermis with biological effects following injection of naked DNA," Nature Genetics; 1995 vol. 10 pp. 161-166.
Herweijer H et al. "Time course of gene expression after plasmid DNA gene transfer to the liver." Journal of Gene Medicine. 2001 vol. 3 No. 3 pp. 280-291.
Hickman MA et al. "Gene expression following direct injection of DNA into liver," Hum Gene Ther; 1994 vol. 5, No. 12 pp. 1477-1483.
Hodges BL et al. "Hydrodynamic delivery of DNA." Expert Opin Biol Ther. 2003 vol. 3 No. 6 pp. 911-918.
Jiao S et al. "Direct gene transfer into nonhuman primate myofibers in vivo," Hum Gene Ther; 1992 vol. 3, No. 1 pp. 21-33.
Jooss K et al. "Immunity to adenovirus and adeno-associated viral vectors: implications for gene therapy." Gene Ther. 2003 vol. 10 No. 11 pp. 955-963.
Kaneda Y et al. "Increased expression of DNA cointroduced with nuclear protein in adult rat liver," Science; 1989 vol. 243, No. 4889 pp. 375-378.
Kaneda Y et al. "Introduction and expression of the human insulin gene in adult rat liver," J Biol Chem; 1989 vol. 264, No. 21 pp. 12126-12129.
Lee BY et al. "Arterial flow in the lower leg correlated with plasma levels of two formulations of papaverine hydrochloride." Angiology 1978 vol. 29 No. 4 pp. 310-319.

(Continued)

*Primary Examiner*—Scott Long
(74) *Attorney, Agent, or Firm*—Kirk Ekena

(57) ABSTRACT

An intravenous delivery method is described that enables delivery of polynucleotides to extravascular cells of a mammalian limb. The method involves the injection of polynucleotides into a distal vein of a limb that is transiently occluded. Polynucleotide delivery is facilitated by rapid injection in sufficient volume to enable extravasation of the solution into surrounding tissue.

30 Claims, 9 Drawing Sheets

OTHER PUBLICATIONS

Lewis D et al. "Efficient delivery of siRNA for inhibition of gene expression in postnatal mice," Nature Genetics; 2002 vol. 32 pp. 107-108.

Liu F et al. "Hydrodynamics-based transfection in animals by systemic administration of plasmid DNA." Gene Therapy; 1999 vol. 6 pp. 1258-1266.

Lowenstein PR et al. "Inflammation and adaptive immune responses to adenoviral vectors injected into the brain: peculiarities, mechanisms, and consequences." Gene Ther. 2003 vol. 10 No. 11 pp. 946-954.

Lu QL et al. "Non-viral gene delivery in skeletal muscle: a protein factory." Gene Ther. 2003 vol. 10 No. 2 pp. 131-142.

Malone RW et al. "Dexamethasone enhancement of gene expression after direct hepatic DNA injection," J Biol Chem; 1994 vol. 269, No. 47 pp. 29903-29907.

McCaffrey AP et al. "RNA interference in adult mice." Nature. 2002 vol. 418 No. 6893 pp. 38-39.

Meyer KB et al. "Intratracheal gene delivery to the mouse airway: characterization of plasmid DNA expression and pharmacokinetics," Gene Ther; 1995 vol. 2, No. 7 pp. 450-460.

Miao CH et al. "Inclusion of the hepatic locus control region, an intron, and untranslated region increases and stabilizes hepatic factor IX gene expression in vivo but not in vitro." Mol Ther. 2000 vol. 1 No. 6 pp. 522-532.

Modig J et al. "Systemic reactions to tourniquet ischaemia." Acta Anaesthesiol Scand. 1978 vol. 22 No. 6 pp. 609-614.

Roberts ML et al. "Stable micro-dystrophin gene transfer using an integrating adeno-retroviral hybrid vector ameliorates the dystrophic pathology in mdx mouse muscle." Hum Mol Genet. 2002 vol. 11 No. 15 pp. 1719-1730.

Sikes ML et al. "In vivo gene transfer into rabbit thyroid follicular cells by direct DNA injection," Hum Gene Ther; 1994 vol. 5, No. 7 pp. 837-844.

Simovic D et al. "Improvement in chronic ischemic neuropathy after intramuscular phVEGF165 gene transfer in patients with critical limb ischemia." Arch Neurol. 2001 vol. 58 No. 5 pp. 761-768.

Soriano P et al. "Targeted and nontargeted liposomes for in vivo transfer to rat liver cells of a plasmid containing the preproinsulin I gene," Proc Natl Acad Sci U S A; 1983 vol. 80, No. 23 pp. 7128-7131.

Stedman HH "Molecular approaches to therapy for Duchenne and limb-girdle muscular dystrophy." Curr Opin Mol Ther. 2001 vol. 3 No. 4 pp. 350-356.

Sun JY et al. "Immune responses to adeno-associated virus and its recombinant vectors." Gene Ther. 2003 vol. 10 No. 11 pp. 964-976.

Svensson EC et al. "Muscle-based gene therapy: realistic possibilities for the future." Mol Med Today. 1996 vol. 2 No. 4 pp. 166-172.

Vale PR et al. "Therapeutic angiogenesis in critical limb and myocardial ischemia." J Interv Cardiol. 2001 vol. 14 No. 5 pp. 511-528.

Vile RG et al. "In vitro and in vivo targeting of gene expression to melanoma cells," Cancer Res; 1993 vol. 53 pp. 962-967.

Wolff JA et al. "Direct gene transfer into mouse muscle in vivo," Science; 1990 vol. 247 pp. 1465-1468.

Wolff JA et al. "Long-term persistence of plasmid DNA and foreign gene expression in mouse muscle," Hum Mol Genet; 1992 vol. 1, No. 6 pp. 363-369.

Yuasa K et al. "Adeno-associated virus vector-mediated gene transfer into dystrophin-deficient skeletal muscles evokes enhanced immune response against the transgene product." Gene Ther. 2002 vol. 9 No. 23 pp. 1576-1588.

Zhang G et al. "Efficient Expression of Naked DNA Delivered Intraarterially to Limb Muscles of Nonhuman Primates." Hum Gene Ther; 2001 vol. 12 pp. 427-438.

Zhang G et al. "High Levels of Foreign Gene Expression in Hepatocytes after Tail Vein Injections of Naked Plasmid DNA," Human Gene Therapy 1999 vol. 10 No. 10 pp. 1735-1737.

Zhang G et al. "Hydroporation as the mechanism of hydrodynamic delivery." Gene Ther. 2004 vol. 11 No. 8 pp. 675-682.

Herweijer H et al. "Progress and prospects: naked DNA gene transfer and therapy" Gene Therapy 2003, vol. 10, p. 453-458.

Zhang G et al. "Surgical procedures for intravascular delivery of plasmid DNA" Methods in Enzymology 2002, vol. 346, p. 125-133.

Hagsrtom JE et al. "A facile nonviral methods for delivering gene and siRNA to skeletal muscle of mammalian limbs" Molecular Therapy 2004, vol. 10, p. 386-398.

Bates M-K et al. "Genetic immunization and antibody generation in research animal by intravenous delivery of plasmid DNA" Journal of Immunotherapy 2005, vol. 28, p. 643.

* cited by examiner

A.

B.

INTRAVENOUS DELIVERY OF POLYNUCLEOTIDES TO CELLS IN MAMMALIAN LIMB

CROSS-REFERENCE TO RELATED APPLICATIONS

This application claims the benefit of prior U.S. Provisional Application Ser. No. 60/473,654 filed on May 28, 2003 and 60/500,211 filed on Sep. 4, 2003.

FIELD OF THE INVENTION

The invention relates to methods for intravenous delivery of polynucleotides to extravascular parenchymal cells in mammal in vivo.

BACKGROUND OF THE INVENTION

Gene therapy is the purposeful delivery of genetic material to cells for the purpose of treating disease or biomedical investigation and research. Gene therapy includes the delivery of a polynucleotide to a cell to express an exogenous nucleotide sequence, to inhibit, eliminate, augment, or alter expression of an endogenous nucleotide sequence, or to produce a specific physiological characteristic not naturally associated with the cell. In some cases, the polynucleotide itself, when delivered to a cell, can alter expression of a gene in the cell. A basic challenge in gene therapy is to develop approaches for delivering genetic information to cells in vivo in a way that is efficient and safe. If genetic material are appropriately delivered they can potentially enhance a patient's health and, in some instances, lead to a cure. Delivery of genetic material to cells in vivo is also beneficial in basic research into gene function as well as for drug development and target validation for traditional small molecule drugs.

Skeletal muscle is an attractive target tissue for gene therapy interventions which aim to treat diseases such as muscular dystrophy or peripheral limb ischemia. Other inborn errors of metabolism and genetic muscle conditions, muscle diseases, muscle atrophy, muscle injury (including sports injuries) and secondary manifestations of muscular dystrophy are also candidates for treatment using gene therapy. In addition to muscle related diseases, other non-muscle conditions may also be treated through gene delivery to skeletal muscle. By delivering genetic material to skeletal muscle cells, muscle tissue could become a modified endocrine tissue. If the delivered gene encodes a protein that is secreted from the muscle cell, diseases such as hemophilia, diabetes, hypercholesterolemia, renal interstitial fibrosis, hypertension, dyslipoproteinemia, chronic renal fibrosis, liver cirrhosis, hyperglycemia, and atherosclerosis may be treated. Gene delivery to muscle cells may also be used to modulate or induce an immune reaction, to treat bone diseases or promote bone healing, or to treat growth plate injuries. While candidate genes have been identified that would likely be therapeutic, current delivery methods have associated problems.

It was first observed that injection of plasmid DNA directly into muscle in vivo enabled expression of foreign genes in the muscle (Wolff et al. 1990). More recently, intra-arterial delivery of polynucleotides to limb skeletal muscle has been shown to be effective (Liu et al. 1999, Lewis et al. 2002, Budker et al. 1996, McCaffrey et al. 2002, Zhang et al. 1999, Budker et al. 1998, Zhang et al. 2001, Liu et al. 2001, Hodges et al. 2003, Eastman et al. 2002). This method provided an improvement over direct muscular injection in affecting delivery of polynucleotides to muscle cells throughout a limb. Transfection efficiencies of >10% of myofibers in multiple muscle groups of the limb were obtained following a single injection into an arterial site (Budker et al. 1998, Zhang et al. 2001). While intra-arterial delivery of polynucleotides to limb skeletal muscle cells has proven to be effective, the procedure is not readily clinically viable. Arterial injections require invasive procedures to access the artery, making questionable whether repeat deliveries are clinically practical. Also, the large injection volumes and high injection rate needed for effective delivery are a cause of concern. Because of the presence of numerous valves in limb veins, it was believed that intravenous injection was not a viable option for delivering polynucleotides to limb muscle in vivo. Injection towards increased branching of the vein, as is done in arterial injection, would be blocked by these valves and would potentially damage the valves.

We now describe an effective in vivo delivery method that overcomes the obstacles presented by valves and uses limb veins for efficient, repeatable, and safe delivery of polynucleotides to skeletal myofibers throughout the limb muscles of mammals. The venous system is an attractive administration route, because like arteries, it is a direct conduit to multiple muscle groups of the limb. Unlike arteries, veins are much easier to access through the skin and there are less potential deleterious consequences relating to vessel damage during injection. In addition, a venous approach provides a more direct conduit to the post-capillary venules, which are more permeable to macromolecules than other parts of the microvasculature in muscle (Palade et al. 1978).

SUMMARY OF THE INVENTION

In one embodiment, a process described for delivering a polynucleotide to a cell in a mammalian limb comprising, impeding blood flow into and/or out of the limb and inserting the polynucleotide in a solution into the lumen of a vein in the limb at a site distal to the occlusion. The polynucleotide is delivered to limb cells distal to the occlusion. The vein may be occluded before, during and after the injection. In a preferred embodiment, said cell is an extravascular cell in a mammalian limb.

In a preferred embodiment, we describe an in vivo process for delivery of a polynucleotide to a parenchymal cell in a mammalian limb comprising: injecting the polynucleotide in a solution into a vein, wherein the volume of the injectate and rate of the injection results in increasing permeability of the vein and venules and increasing the volume of extravascular fluid in the target tissue. Increasing vein permeability and the volume of extravascular fluid in the target tissue may further comprise blocking the flow of fluid through one or more vessels into and/or out of a target tissue or area. The solution may additionally contain a compound or compounds which may or may not associate with the polynucleotide and may aid in delivery.

In a preferred embodiment, the process further comprises administration of at least one anesthetic or analgesic drug or adjuvant. Administration of anesthetics or analgesic lessens potential discomfort or pain experienced by the mammal during or after the procedure. Examples of such drugs lidocarine, NSAIDs, clonidine, ketamine, neuromuscular blockers, and immunsuppressants.

In a preferred embodiment, a method is described for increasing the transit of a polynucleotide out of a vessel and into a surrounding tissue in a mammal in vivo comprising: injecting a volume of injection solution containing the polynucleotide into a vein of the target tissue, thereby forcing fluid out of the vein and into the extravascular space. The target tissue is the tissue from which the vein drains blood. The injection solution may further contain a compound or compounds which may aid in delivery and may or may not associate with the polynucleotide.

In a preferred embodiment, an in vivo process is described for delivering a polynucleotide to a mammalian cell comprising: inserting the polynucleotide in a solution into a vein while impeding or occluding fluid flow through one or more vessels proximal to the point of injection and the target tissue. The occlusion may be an occlusion that exists in the mammal, such as a clot, or the occlusion may be applied. The process includes impeding fluid flow through veins or arteries of the target tissue by applying external compression against mammalian skin. This compression includes applying a cuff over the skin, such as a sphygmomanometer (or other device with a bladder than is inflated) or a tourniquet. Fluid flow through a vessel may also be impeded by clamping the vessel or by a balloon catheter placed within the vessel. The vessels are occluded for a period of time necessary to deliver the polynucleotide without causing ischemic damage to the tissue. The solution is injected into the limb vein distal to the occlusion. The solution is injected using an injection device selected from the group comprising: catheter, syringe needle, cannula, stylet, balloon catheter, multiple balloon catheter, single lumen catheter, and multilumen catheter.

The cell may be selected from the groups consisting of: skeletal muscle cells (myofiber, myocytes) bone cells (osteocytes, osteoclasts, osteoblasts), bone marrow cells, stroma cells, joint cells (synovial and cartilage cells), connective tissue cells (fibroblasts, fibrocytes, chondrocytes, mesenchyme cells, mast cells, macrophages, histiocytes), cells in tendons cells in the skin and cells in the lymph nodes.

The described method can be used to deliver a polynucleotide to a mammalian cell for the purpose of altering the endogenous properties of the cell, for example altering the endogenous properties of the cell for therapeutic purposes, for augmenting function, for facilitating pharmaceutical drug discovery, for facilitating drug target validation or for investigating gene function (i.e., research).

Further objects, features, and advantages of the invention will be apparent from the following detailed description when taken in conjunction with the accompanying drawings.

DETAILED DESCRIPTION OF THE INVENTION

The described invention provides methods for delivery of polynucleotides to extravascular cells of mammalian limbs. More specifically, the invention relates to the use of the venous system to deliver polynucleotides to cells outside of the vascular system whereby the polynucleotides are injected into a vein in the limb in an anterograde direction (in the direction of normal blood flow). Intravenous delivery of polynucleotides provides a number of advantages. Venous injection is associated with less risk than arterial injection. Some veins are located nearer the surface than arteries and are thus more accessible than arteries. Therefore, the venous system is more readily accessible to both initial (single) and repeat deliveries. In addition, venous injection combined with the use of a cuff for impeding blood flow provides a non-surgical method for polynucleotide delivery. If injury does occur to a vein during a procedure, the injury is less problematic than injury to an artery. Vessels of the venous system also have reduced vessel wall thickness relative to comparable arterial vessels and they can be made more permeable than the arterial system thus allowing increased delivery to extravascular locations. For certain clinical indications, where the arterial system displays vascular pathology (arteriosclerosis, atherosclerosis, and single or multiple partial or total occlusions), the venous system represents a more attractive delivery conduit to deliver the polynucleotide to the extravascular region of interest, including skeletal muscle cells.

Figure 1A:
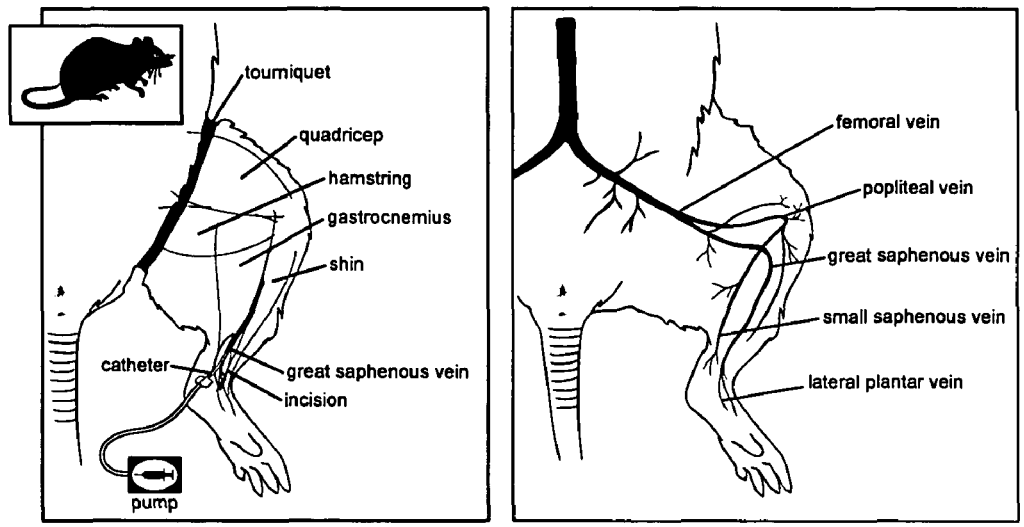
FIG. 1A-1C. Schematic diagram of catheter-mediated intravenous injection of nucleic acids into mammalian limb A) IV delivery to distal hind limb of rats. B) IV delivery to distal hind limb of primate. C) IV delivery to distal hind limb of human. Left panel in each illustrates major veins of the limb. Occlusion sites and injection sites shown in the diagrams are for illustrative purposes. Different occlusion and injection sites are possible as indicated in the description and examples.
Figure 1B:
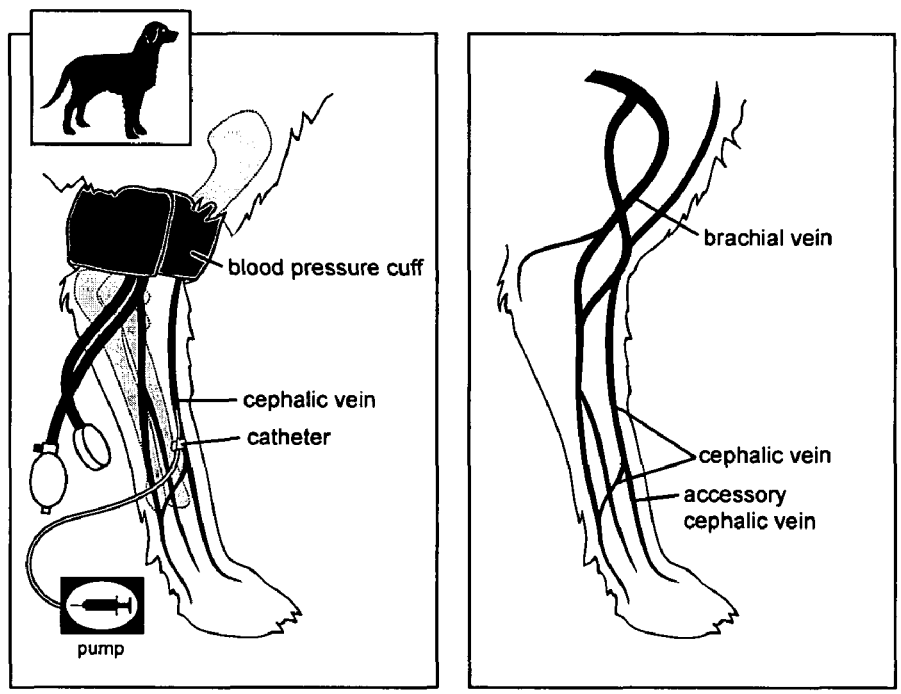
Figures 1C, 1D:
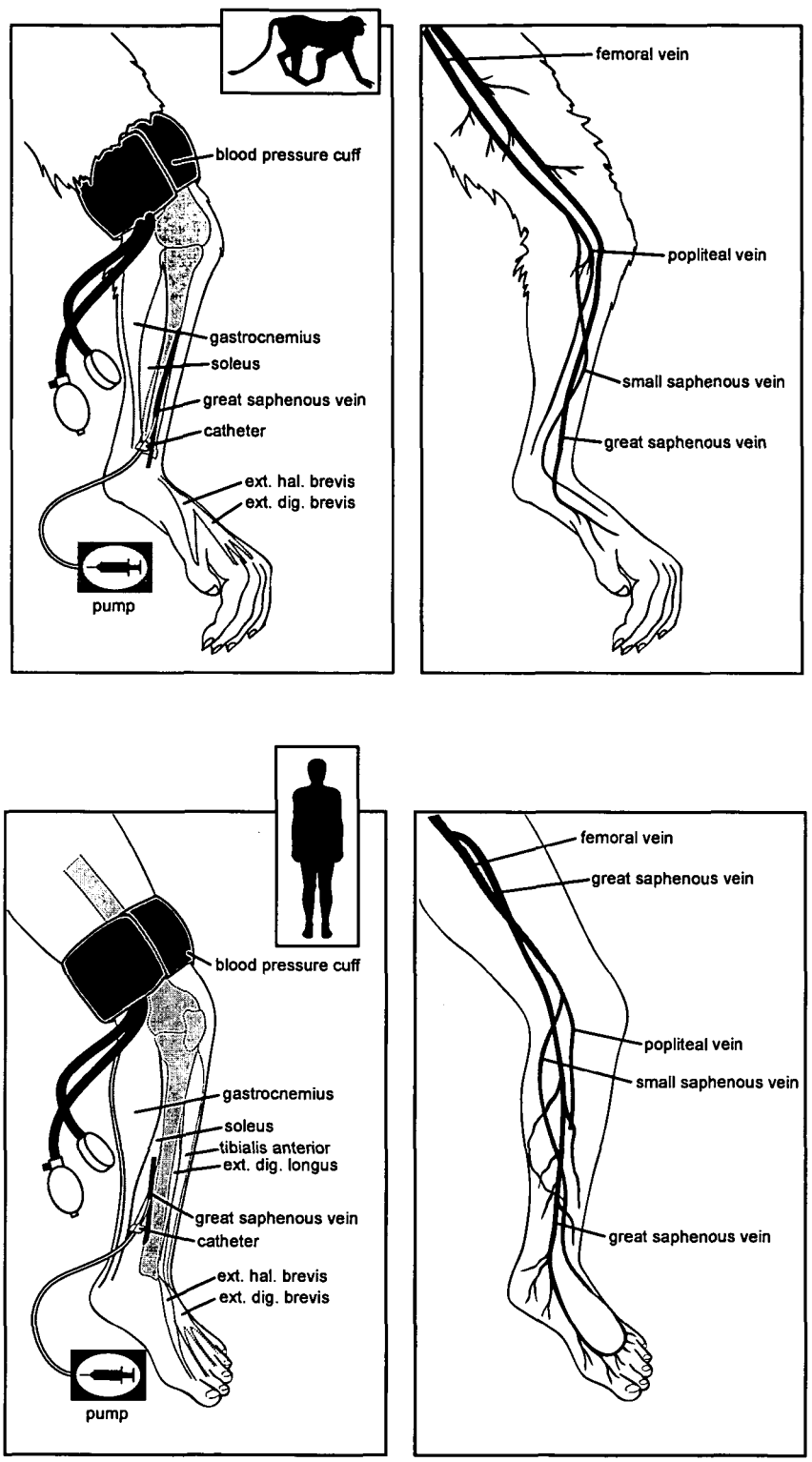

The intravenous delivery method comprises: impeding blood flow out of a target limb, inserting into a vein in the limb, distal to the occlusion, an injection device, and injecting into the vein in an antegrade direction a solution containing the polynucleotide (FIG. 1). The injection volume and injection rate are dependent upon: the size of the animal, the size of the vein into which the solution is injected, and the size and/or volume of the target tissue. Larger injection volumes and/or higher injection rates are required for larger target or limb sizes. For delivery to larger animals, injection of larger volumes is expected. One method of determining limb size is through volume displacement measurement or through MRI scan, which can be used to determine muscle mass. The precise volume and rate of injection into a particular vein, for delivery to a particular target tissue of a given mammal species, may be determined empirically. Cells located distal to the occlusion are those cells located between the occlusion and the end of the limb that is farther from the heart. For injection into a vein of the hand, foot or joint, the solution may be injected in a retrograde direction. For delivery to an isolated portion of a limb, blood flow to the limb section may be occluded both proximal and distal to the target area. The described methods provide for more even distribution of polynucleotides to cells throughout a limb or target tissue than is possible with direct intramuscular injections.

A needle, cannula, catheter or other injection device may be used to inject the polynucleotide into the vein. Single and multi-port injectors may be used, as well as single or multi-balloon catheters and single and multilumen injection devices. A catheter can be inserted at a distant site and threaded through the lumen of a vein so that it resides in or near a target tissue. The injection can also be performed using a needle that traverses the skin and enters the lumen of a vein. Occlusion of vessels, by balloon catheters, clamps, or cuffs can limit or define target area. The described intravenous processes require that blood flow be impeded for substantially less time than is required to cause tissue damage by ischemia.

One method for occluding fluid flow is the application of an external cuff. The term cuff means an externally applied device for impeding fluid flow to and from a mammalian limb. The cuff applies compression around the limb such that vessels, in an area underneath the cuff, are forced to occlude an amount sufficient to impede fluid from flowing through the vessels at a normal rate. One example of a cuff is a sphygmomanometer, which is normally used to measure blood pressure. Another example is a tourniquet. A third example is a modified sphygmomanometer cuff containing two air bladders such as is used for intravenous regional anesthesia (i.e. Bier Block). Double tourniquet, double cuff tourniquet, oscillotonometer, oscillometer, and haemotonometer are also examples of cuffs. A sphygmamanometer can be inflated to a pressure above the systolic blood pressure, above 500 mm Hg or above 700 mm Hg or greater than the intravascular pressure generated by the injection.

Inserting an appropriate volume of injection solution into a peripheral limb vein at an appropriate rate, together with proximal occlusion of vessels in the limb increases permeability of vasculature in the limb to the injection solution and the polynucleotides therein. Permeability is the propensity for macromolecules to move out of a vessel and enter the extravascular space. Occluding blood flow can be done by blocking blood flow to and from the entire limb or by occluding specific vessels. For occluding the entire limb, a cuff can be used. Vessels are partially or totally occluded for a period of time sufficient to allow delivery of a polynucleotide present in the injection solution. The occlusion may be released immediately after injection or may be released only after a determined length of time which does not result in tissue damage due to ischemia. The polynucleotides may be naked polynucleotides or they may be in association with components that aid in delivery, such as non-viral transfection agents. It is also possible to deliver other macromolecules, such as proteins or viral vectors, to extravascular cells.

Because vasculature may not be identical from one individual to another, methods may be employed to predict or control appropriate injection volume and rate. Injection of iodinated contrast dye detected by fluoroscopy can aid in determining vascular bed size. MRI can also be used to determine bed size. Also, an automatic injection system can be used such that the injection solution is delivered at a preset pressure or rate. For such a system, pressure may be measured in the injection apparatus, in the vessel into which the solution is injected, in a branch vessel within the target tissue, or within a vein or artery within the target tissue.

Other agents known in the art may be used to further increase vessel permeability, including drugs or chemicals and hypertonic solutions. Drugs or chemicals can increase the permeability of the vessel by causing a change in function, activity, or shape of cells within the vessel wall; typically interacting with a specific receptor, enzyme or protein of the vascular cell. Other agents can increase permeability by changing the extracellular connective material. Examples of drugs or chemicals that may be used to increase vessel permeability include histamine, vascular permeability factor (VPF, which is also known as vascular endothelial growth factor, VEGF), calcium channel blockers (e.g., verapamil, nicardipine, diltiazem), beta-blockers (e.g., lisinopril), phorbol esters (e.g., PKC), ethylenediamine-tetraacetic acid (EDTA), adenosine, papaverine, atropine, and nifedipine. The permeability enhancing drug or chemical may be present in the polynucleotide-containing injection solution. An efflux enhancer solution, a solution containing a permeability enhancing drug or chemical, may also be injected into the vein prior to injection of the solution containing the polynucleotide. Hypertonic solutions have increased osmolarity compared to the osmolarity of blood thus increasing osmotic pressure and causing cells to shrink. Typically, hypertonic solutions containing salts such as NaCl or sugars or polyols such as mannitol are used. Delivery might also be enhanced by pharmacologic agents that cause vasoconstriction or vasodilation such as catecholamines, epinephrine, norepineprhine, dopamine, dobutamine, adrenergic blockers (such as Caldura (Pfizer), dibensyline (Wellspring), Hytrin (Abbott), and Minipress (Pfizer)), adrenergic stimulants (aldoclor (Merck), catapres (oerhringer-Ingelheim) and Clorpres (Bertek)), angiotensin converting enzyme (ACE) inhibitors, diuretics, angiotensin II receptor antagonists, beta adrenergic blockers. Agents that block or prevent blood clotting (or digest blood clots) such as heparin, thrombolytic agents (urokinase, Abbokinase), tissue plasminogen activators (Tenectcplase, TNKase, Alteplase, Activase I.V.), natriuretic peptides, vasopressors, and endothelin receptor antagonists (bosentan) may also be injected into the vessel. Enzymes such as collagenases, hyaluronidases, and heparinases may also be used to improve delivery.

Physical applications of cold, heat, electromagnetic radiation, electric currents, voltages and ultrasound could also be used to improve delivery.

Physical forces can also be applied to the limb to aid in delivery of the polynucleotides. These physical forces include heat, cold, electromagnetic radiation such as microwave or infrared radiation, ultrasound, electric current and voltage.

The polynucleotide is injected in a pharmaceutically acceptable solution. Pharmaceutically acceptable refers to those properties and/or substances which are acceptable to the mammal from a pharmacological/toxicological point of view. The phrase pharmaceutically acceptable refers to molecular entities, compositions and properties that are physiologically tolerable and do not typically produce an allergic or other untoward or toxic reaction when administered to a mammal. Preferably, as used herein, the term pharmaceutically acceptable means approved by a regulatory agency of the Federal or a state government or listed in the U.S. Pharmacopeia or other generally recognized pharmacopeia for use in animals, and more particularly in humans.

The described method is shown to be effective for delivering polynucleotides to limb muscle cells in mouse, rat, rabbit, dog, and nonhuman primate. Delivery to other cells in the limb, including cells of the joint (including synovial, cartilage cells, and capsular cells) and bone, and bone marrow (including hematopoietic and hematopoietic stem cells and bone marrow stromal cells), is also possible. By increasing the amount of polynucleotide injected and the volume of injection, the method described for IV delivery of polynucleotides to limb cells in small mammals such as rats is readily adapted to use in larger animals. Injection rate may also be increased for delivery to larger mammals. Conversely, for delivery to smaller animals, the injection volume and/or rate is reduced. For example, for delivery to rat hind limb (150 g animal total weight), injection of 0.2-3 ml injection solution at a rate of 0.5-25 ml/min into the saphenous vein results in delivery of polynucleotides to multiple muscle cells throughout the limb. For delivery to beagle dog (~9.5 kg total weight) forelimb, injection of 36-40 ml injection solution at a rate of 2 ml/sec into a limb vein results in delivery of polynucleotides to multiple muscle cells throughout the limb. For delivery to rhesus monkey limb, injection of 40-100 ml injection solution at a rate of 1.7-2 ml/sec into a limb vein results in delivery of polynucleotides to multiple muscle cells throughout the limb. This volume corresponds to from about 0.2 to about 0.6 ml of injection solution per ml of displaced target limb volume in rhesus monkey. Target limb volume is the volume of the limb or portion of the limb distal to the vein occlusion or isolated by the vessel occlusion. The intravenous injection method results in highly efficient gene delivery to nearly all muscle groups of the limb distal to the occlusion following a single injection. It is particularly noteworthy that the level of transgene expression that can be achieved using this procedure does not diminish as the procedure is scaled up to larger mammals. In contrast, direct intramuscular injections of plasmid DNA results in high expression levels per gram of muscle in rodents but very low expression levels per gram of muscle in primates (Jiao et al. 1992). Because the method is readily adapted to use in rats, dogs, and nonhuman primates, it is expected that the method is also readily adapted to use in other mammals, including humans.

The described process may also be used repetitively in a single mammal. Multiple injections may be used to provide delivery to additional tissues, to increase delivery to a single tissue, or where multiple treatments are indicated. Multiple injections may be performed in different limbs of the same animal, within the same limb of the animal, within the same vein of the animal, within different veins in the animal (in the same or different limbs). The site of vessel occlusion may also be the same or different for multiple injections in the same animal.

The polynucleotide may be inserted into any vein present in the limb distal to the site of occulsion. A preferred vein consists of a superficial vein. Limb veins may be selected from the list comprising: cephalic vein, median vein, median cephalic, median basilica, brachial vein, basilic vein, interosseous vein, radial vein, ulnar vein (anterior, posterior, common), deep palmar veins, great saphenous vein (medial saphenous vein, v. saphena magna, internal saphenous vein, long saphenous vein), lesser saphenous vein, small saphenous vein (lateral saphenous vein, external saphenous vein, v. saphena parca, short saphenous vein), anterior tibial vein, posterior tibial vein, peroneal vein, popliteal vein, plantar vein (medial and lateral), dorsal venous arch, dorsal digital vein, dorsal metacarpal vein and dorsal pedis vein.

It is predicted that the described methods may be combined with other delivery vehicles or vectors or other delivery enhancing groups. Such delivery vehicles and groups comprise: transfection reagents, viral vectors, non-viral vectors, lipids, polymers, polycations, amphipathic compounds, targeting signals, nuclear targeting signals, and membrane active compounds. The composition of the injection solution can depend on the nature of the molecule or complex that is to be delivered. Certain complexes may be delivered more efficiently using low salt injection solutions. The use or hypertonic or hypotonic injection solutions or the use of vasodilators in the injection solution may further enhance delivery.

Delivery of a gene to a cell that expresses a protein not previously expressed in the mammal can result in the induction of an immune response directed against the newly expressed protein. Also, the polynucleotide itself, or other potential components of the injection solution, may illicit an immune response. Therefore it may be beneficial to provide immunosuppressive drugs to the mammal. Suppression of immune response to an expressed gene can prolong expression of the gene. Immunosuppressive drugs can be given before, during, or after injection of the polynucleotide. Immunosuppression can be of short term duration (less than 3 months) or long term duration.

A polynucleotide can be delivered to a limb cell to study gene function. Delivery of a polynucleotide to a limb cell can also have potential clinical applications. Clinical applications include treatment of muscular dystrophies, circulatory disorders, endocrine disorders, immune modulation and vaccination, and metabolic disorders (Baumgartner et al. 1998, Blau et al. 1995, Svensson et al. 1996, Baumgartner et al. 1998, Vale et al. 2001, Simovic et al. 2001). The ability to deliver genes effectively to muscles of the distal limb makes this approach clinically attractive for preserving hand or foot function in patients with muscular dystrophy or for increasing distal blood flow in patients with peripheral artery disease.

In a preferred embodiment, the process may be used to deliver a therapeutic polynucleotide to a muscle cell for the treatment of vascular disease or occlusion. The delivered polynucleotide can express a protein or peptide that stimulates angiogenesis, vasculogenesis, arteriogenesis, or anastomoses to improve blood flow to a tissue. The gene may be selected from the list comprising: VEGF, VEGF II, VEGF-B, VEGF-C, VEGF-D, VEGF-E, $VEGF_{121}$, $VEGF_{138}$, $VEGF_{145}$, $VEGF_{165}$, $VEGF_{189}$, $VEGF_{206}$, hypoxia inducible factor 1α (HIF1α), endothelial NO synthase (eNOS), iNOS, VEFGR-1 (Flt1), VEGFR-2 (KDR/Flk1), VEGFR-3 (Flt4), neuropilin-1, ICAM-1, factors (chemokines and cytokines) that stimulate smooth muscle cell, monocyte, or leukocyte migration, anti-apoptotic peptides and proteins, fibroblast growth factors (FGF), FGF-1, FGF-1b, FGF-1c, FGF-2, FGF-2b, FGF-2c, FGF-3, FGF-3b, FGF-3c, FGF-4, FGF-5, FGF-7, FGF-9, acidic FGF, basic FGF, hepatocyte growth factor (HGF), angiopoietin 1 (Ang-1), angiopoietin 2 (Ang-2), CTGF-2 (connective tissue growth factor), Platelet derived growth factors (PDFGs), PDGF-BB, monocyte chemotactic protein-1, granulocyte macrophage-colony stimulating factor, insulin-like growth factor-1 (IGF-1), IGF-2, early growth response factor-1 (EGR-1), ETS-1, human tissue kallikrein (HK), matrix metalloproteinase, chymase, urokinase-type plasminogen activator and heparinase. For proteins and peptides that are secreted, the gene may contain a sequence that codes for a signal peptide. The delivered polynucleotide can also suppress or inhibit expression of an endogenous gene or gene product that inhibits angiogenesis, vasculogenesis, arteriogenesis or anastomosis formation. Multiple polynucleotides or polynucleotides containing more than one therapeutic gene may be delivered using the described process. The gene or genes can be delivered to stimulate vessel development, stimulate collateral vessel development, promote peripheral vascular development, or to improve blood flow in a muscle tissue. The gene or genes can also be delivered to treat peripheral circulatory disorders, limb ischemia, arterial occlusive disease, peripheral arterial occlusive disease, vascular insufficiency, vasculopathy, arteriosclerosis obliterans, thromboangiitis obliterans, atherosclerosis, aortitis syndrome, Behcet's disease, collagenosis, ischemia associated with diabetes, claudication, intermittent claudication, Raynaud disease, cardiomyopathy or cardiac hypertrophy. The polynucleotide can be delivered to a muscle cell that is suffering from ischemia or a normal muscle cell. The polynucleotide can also be delivered to a cells in a tissue that is at risk of suffering from ischemia or a vascular disease or disorder.

In a preferred embodiment, the methods may be used for delivery of polynucleotides to limb muscle cells for the treatment of muscular dystrophy (MD), for secondary manifestations of muscular dystrophy, or for other muscular atrophy or injury. The defective genes that cause MD are known for many forms of the disease. These defective genes either fail to produce a protein product, produce a protein product that fails to function properly, or produce a dysfunctional protein product that interferes with the proper f unction of the cell. The polynucleotide may encode a therapeutically functional protein or a polynucleotide that inhibits production or activity of a dysfunctional protein. Such genes may be selected from the list comprising: dystrophin (Duchenne's and Becker MD); dystrophin-associated glycoproteins (β-sarcoglycan and β-sarcoglycan, limb-girdle MD 2E and 2F; α-sarcoglycan and γ-sarcoglycan, limb-girdle MD 2D and 2C), utrophin, calpain (autosomal recessive limb-girdle MD type 2A), caveolin-3 (autosomal-dominant limb-girdle MD), laminin-alpha2 (merosin-deficient congenital MD), fukutin (Fukuyama type congenital MD) and emerin (Emery-Dreifuss MD) or therapeutic variation of these proteins. A polynucleotide expressing a protein beneficial to a patient suffering from muscular disease or injury or booster genes aimed at alleviating secondary defects of muscle disease may also be delivered to muscle cells of the patient. Such genes may be selected from the list comprising: mini-agrin (to promote basement membrane formation), utrophin, laminin α2, α7 integrins, GalNac transferase, and ADAM12 (to promote cell adhesion and muscle stability), calpastatin (to protect against muscle necrosis), nitric oxide synthase (to ease inflammation), ADAM12, IGF-I, dominant negative myostatin and myostatin inhibitors (to promote muscle regeneration and reduce fibrosis), TGF-β (to regulate muscle mass), Nitric Oxide Synthase (to reduce inflammation), actin, titin, muscle creatine kinase, troponin, growth factors (human growth factor and human growth hormone releasing hormone, and vascular endothelial growth factor (VEGF)), insulin, and anti-inflammatory genes. Polynucleotides such as siRNAs and antisense oligonucleotides may also be delivered to create a myostatin blockade or to inhibit myostatin synthesis (to promote muscle growth), inhibit myogenin production (to increase muscle size) or to modify splicing of a defective endogenous gene.

In a preferred embodiment, polynucleotides may be delivered to limb skeletal muscle cells and other extravascular or parencyhmal cells to provide for expression of a secreted protein. Although muscle is not generally regarded as a secretory tissue, products from genes delivered to muscle cells can enter the systemic circulation. The possibility exists, therefore, of using this approach to alter levels of endocrine and paracrine factors and other therapeutic proteins. In this way, muscle is used as a bioreactor for transgene production, to generate a protein that is secreted for a systemic effect. As a therapeutic procedure, this method has an advantage over the administration of the peptide/protein, which has a relatively short half-life and requires repeated injections. (Goldspink 2003). Endocrine disorders, such as growth hormone deficiency, anemia and others, neurotrophic disorders, including diabetic neuropathy and peripheral neuropathy, circulatory disorders and metabolic disorders are examples of diseases that may be treated using gene transfer to muscle. Genes that encode potentially therapeutic proteins may be selected from the list comprising: EL-10, soluble p75 tumor necrosis factor receptor-Fc fusion protein, interleukin-1 receptor antagonist (IL-RA), and TNFα antagonists for treatment of arthritis; modified insulin, preproinsulin and modified preproinsulin genes for treatment of diabetes; apolipoprotein E and adiponectin for treatment or prevention of cholesterol-related diseases such as hypercholesterolemia and atheroschlerosis; glucokinase or glucose transporter for treatment of hyperglycemia; hepatocyte growth factor and angiotensin II blockers for interstitial kidney disease, renal interstitial fibrosis and chronic renal fibrosis; IGF1 for liver cirrhosis, muscle disease and muscle injury, neuropathy, etc; clotting factors including factor IX for hemophilia; interferon alpha and cytokines IL-2 and IL12 to treat cancer or hepatitis; osteoinductive factors and growth factors such as bone morphogenic protein-2 to treat bone disease and improve fracture healing; cytokines and cytokine inhibitors to treat auto-immune disorders or to modify immune reaction; hematopoietic factors and erythropoietin (Epo) for treatment of anemia; growth hormone and mechano growth factor to induce muscle growth/hypertrophy and to increase muscle mass; α-galactosidase for treatment of Fabry's disease; IGF-1 and bone morphogenic protein-2 (BMP-2) for treatment of growth plate injuries; alpha-antitrypsin to treat emphysema or prevent lung disease; granulocyte macrophage colony stimulating factor for treatment of cancer and other nerve growth factors, autocrine factors, growth factors and secretagogues.

Gene transfer to muscle can also be used to treat metabolic diseases such as obesity and diabetes. For example, obesity can be treated by delivering the gene for leptin or diabetes can be treated by delivering a gene for insulin and insulin genes with modifications for furin cleavage and regulated expression. Other inborn errors of metabolism that may be treated by delivering genes encoding secreted proteins to muscle include: cystic fibrosis, phenylketonuria (PKU), tyrosinemia, urea cycle defects, disorders of amino acid metabolism (such as propionic acidiruia, methylmalonic aciduria), disorders of fat and fatty acid metabolism, disorders of carbohydrate metabolism (galactosema) glycogen storage defects (including Pompe disease and McArdle disease), lysosomal storage disorders, mitochondrial disorders, respiratory chain defects, and bilirubin metabolic defects (Crigler-Najjar Syndrome type I and II, Gilbert syndrome, Dubin-Johnson syndrome, Rotor syndrome). Lipoprotein levels may by modulated by delivering genes for low density lipoprotein (LDL) receptor, apolipoprotein A, apolipoprotein E or transcription factors that regulate expression of these genes or to raise high density lipoprotein (HDL) levels.

A therapeutic effect of the protein in attenuating or preventing the disease state can be accomplished by the protein either staying within the cell, remaining attached to the cell in the membrane or being secreted and dissociating from the cell where it can enter the general circulation and blood. Proteins on the membrane can have a therapeutic effect by providing a receptor for the cell to take up a protein or lipoprotein. For example, the low density lipoprotein (LDL) receptor could be expressed in hepatocytes and lower blood cholesterol levels and thereby prevent atherosclerotic lesions that can cause strokes or myocardial infarction. Therapeutic proteins that stay within the cell can be enzymes that clear a circulating toxic metabolite as in phenylketonuria. They can also cause a cancer cell to be less proliferative or cancerous (e.g. less metastatic). A protein within a cell could also interfere with the replication of a virus.

We have disclosed gene expression achieved from reporter genes in specific tissues. Levels of a gene product, including reporter (marker) gene products, are measured which then indicate a reasonable expectation of similar amounts of gene expression by transfecting other polynuleotides. Levels of treatment considered beneficial by a person having ordinary skill in the art differ from disease to disease, for example: Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. Thus, an increase from 1% to 2% of the normal level of circulating factor in severe patients can be considered beneficial. Levels greater than 6% prevent spontaneous bleeds but not those secondary to surgery or injury. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels. Thus, reporter or marker genes such as the genes for luciferase and β-galactosidase serve as useful paradigms for expression of intracellular proteins in general. Similarly, reporter or marker genes secreted alkaline phosphatase (SEAP) serve as useful paradigms for secreted proteins in general.

In a preferred embodiment, polynucleotides may be delivered to limb skeletal muscle cells to provide for expression of a peptide or protein antigen. We show that intravenous administration of a polynucleotide-containing solution results in delivery of the polynucleotide to nonvascular parenchymal cells, expression of a gene encoded by the polynucleotide in the cells, and induction of an immune response in the mammal. The polynucleotide can encode a peptide or protein antigen to generate an immune response in the animal. The described process can be used for the production of antibodies in a mammal, to provide a vaccine, or to provide a therapeutic response, such as to cancer or infection.

The delivery method can also be used to deliver cells such as myoblasts and hematopoietic stem cells. The cells can be genetically modified to produce a therapeutic protein.

Definitions:

Polynucleotide—The term polynucleotide, or nucleic acid or polynucleic acid, is a term of art that refers to a polymer containing at least two nucleotides. Nucleotides are the monomeric units of polynucleotide polymers. Polynucleotides with less than 120 monomeric units are often called oligonucleotides. Natural nucleic acids have a deoxyribose- or ribose-phosphate backbone. An artificial or synthetic polynucleotide is any polynucleotide that is polymerized in vitro or in a cell free system and contains the same or similar bases but may contain a backbone of a type other than the natural ribose-phosphate backbone. These backbones include: PNAs (peptide nucleic acids), phosphorothioates, phosphorodiamidates, morpholinos, and other variants of the phosphate backbone of native nucleic acids. Bases include purines and pyrimidines, which further include the natural compounds adenine, thymine, guanine, cytosine, uracil, inosine, and natural analogs. Synthetic derivatives of purines and pyrimidines include, but are not limited to, modifications which place new reactive groups such as, but not limited to, amines, alcohols, thiols, carboxylates, and alkylhalides. The term base encompasses any of the known base analogs of DNA and RNA. The term polynucleotide includes deoxyribonucleic acid (DNA) and ribonucleic acid (RNA) and combinations of DNA, RNA and other natural and synthetic nucleotides.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. Altering gene expression may comprise: altering splicing of an RNA, affecting mRNA levels, and altering gene expression through binding to transcription factors. A polynucleotides can also alter the sequence of a polynucleotide in a cell. This would include polynucleotides that alter the sequence of chromosomal DNA, cellular RNA, viral DNA, viral RNA. Altering the sequence of a polynucleotide in a cell includes altering the sequence through gene conversion or recombination. Chimeroplasts (hybrid molecules of RNA and DNA) and single stranded polynucleotides have been used to alter chromosomal DNA sequences.

A polynucleotide-based gene expression inhibitor comprises any polynucleotide containing a sequence whose presence or transcription in a cell causes sequence-specific degradation or inhibition of the function, transcription, or translation of a gene. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15-50 base pairs and preferably 19-25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise sequence that is complimentary to an gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Expression cassette: The term expression cassette refers to a natural or recombinantly produced nucleic acid molecule that is capable of expressing a gene or genetic sequence in a cell. An expression cassette typically includes a promoter (allowing transcription initiation), and a sequence encoding one or more proteins or RNAs. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences. Optionally, the expression cassette may include a gene or partial gene sequence that is not translated into a protein. The nucleic acid can effect a change in the DNA or RNA sequence of the target cell. This can be achieved by hybridization, multi-strand nucleic acid formation, homologous recombination, gene conversion, RNA interference or other yet to be described mechanisms.

The term gene generally refers to a nucleic acid sequence that comprises coding sequences necessary for the production of a nucleic acid (e.g., siRNA) or a polypeptide or precursor. A polypeptide can be encoded by a full length coding sequence or by any portion of the coding sequence so long as the desired activity or functional properties (e.g., enzymatic activity, ligand binding, signal transduction) of the full-length polypeptide or fragment are retained. The term also encompasses the coding region of a gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term gene encompasses synthetic, recombinant, cDNA and genomic forms of a gene. A genomic form or clone of a gene contains the coding region interrupted with non-coding sequences termed introns, intervening regions or intervening sequences. Introns are segments of a gene which are transcribed into nuclear RNA. Introns may contain regulatory elements such as enhancers. Introns are removed or spliced out from the nuclear or primary transcript; introns therefore are absent in the mature RNA transcript. Components of a gene also include, but are not limited to, promoters, enhancers, transcription factor binding sites, polyadenylation signals, internal ribosome entry sites, silencers, insulating sequences, matrix attachment regions. Non-coding sequences influence the level or rate of transcription and/or translation of the gene. Covalent modification of a gene may influence the rate of transcription (e.g., methylation of genomic DNA), the stability of mRNA (e.g., length of the 3' polyadenosine tail), rate of translation (e.g., 5' cap), nucleic acid repair, nuclear transport, and immunogenicity. Gene expression can be regulated at many stages in the process. Up-regulation or activation refers to regulation that increases the production of gene expression products (i.e., RNA or protein), while down-regulation or repression refers to regulation that decrease production. Molecules (e.g., transcription factors) that are involved in up-regulation or down-regulation are often called activators and repressors, respectively.

It may be desirable to regulate expression of the delivered polynucleotide using regulated promoters. Regulated promoters may be inducible or repressible. Regulated gene expression systems may be selected from the list comprising: drug-dependent gene regulation, tetracycline/doxycycline-inducible, tetracycline/doxycycline-repressible, rapamycin-inducible, β-galactoside, streptogramin-regulated, bacterial repressor protein, antiprogestin-inducible GeneSwitch® (Valentis, Inc., induced by mifepristone), nuclear hormone receptor ligand binding domain (antiprogestin-, antiestrogen-, ecdysteroid-, glucocorticoid-responsive), heterodimeric protein, metabolic regulated, hypoxia responsive, and glucose responsive systems. Some of these systems are regulated by proteins naturally occurring in mammalian cells while others require co-delivery of a gene encoding a transcription activator or repressor.

It may also be desirable for the delivered polynucleotide to be expressed from a muscle specific promoter. Muscle specific promoters may be selected from the list comprising: muscle creatine kinase (MCK), myosin light chain, myosin light chain 3F, desmin, alpha-actin, enolase, utrophin, dystrophin, sarcoglycan and other dystrophin-associated glycoprotein promoters. Still other transcription elements that function in muscle include: actin and β-actin promoters, E-box elements, MEF-2 elements, TEF-1 elements, SRE sites, myogenin enhancer sequences, and viral promoters such as CMV and SV40.

A biologically active compound is a compound having the potential to react with biological components. More particularly, biologically active compounds utilized in this specification are designed to change the natural processes associated with a living cell. For purposes of this specification, a cellular natural process is a process that is associated with a cell before delivery of a biologically active compound. Biologically active compounds may be selected from the group comprising: pharmaceuticals, proteins, peptides, polypeptides, hormones, cytokines, antigens, viruses, oligonucleotides, nucleic acids, and synthetic polymers such as polypyroles could also be delivered.

Transfection—The process of delivering a polynucleotide to a cell has been commonly termed transfection or the process of transfecting and also it has been termed transformation. The term transfecting as used herein refers to the introduction of a polynucleotide or other biologically active compound into cells. The polynucleotide may be used for research purposes or to produce a change in a cell that can be therapeutic. The delivery of a polynucleotide for therapeutic purposes is commonly called gene therapy. The delivery of a polynucleotide can lead to modification of the genetic material present in the target cell. The term stable transfection or stably transfected generally refers to the introduction and integration of an exogenous polynucleotide into the genome of the transfected cell. The term stable transfectant refers to a cell which has stably integrated the polynucleotide into the genomic DNA. Stable transfection can also be obtained by using episomal vectors that are replicated during the eukaryotic cell division (e.g., plasmid DNA vectors containing a papilloma virus origin of replication, artificial chromosomes). The term transient transfection or transiently transfected refers to the introduction of a polynucleotide into a cell where the polynucleotide does not integrate into the genome of the transfected cell. If the polynucleotide contains an expressible gene, then the expression cassette is subject to the regulatory controls that govern the expression of endogenous genes in the chromosomes. The term transient transfectant refers to a cell which has taken up a polynucleotide but has not integrated the polynucleotide into its genomic DNA.

Transfection Agent—A transfection agent, or transfection reagent or delivery vehicle, is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, histone proteins, polyethylenimine, polylysine, and polyampholyte complexes. It has been shown that cationic proteins like histones and protamines, or synthetic polymers like polylysine, polyarginine, polyornithine, DEAE dextran, polybrene, and polyethylenimine may be effective intracellular in vitro delivery agents. Typically, the transfection reagent has a component with a net positive charge that binds to the oligonucleotide's or polynucleotide's negative charge. For delivery in vivo, complexes made with sub-neutralizing amounts of cationic transfection agent may be preferred. Non-viral vectors is include protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associated functional groups with a polynucleotide. Functional groups include cell targeting signals, nuclear localization signals, compounds that enhance release of contents from endosomes or other intracellular vesicles (such as membrane active compounds), and other compounds that alter the behavior or interactions of the compound or complex to which they are attached (interaction modifiers).

The cell targeting signal can be cell receptor ligands, such as proteins, peptides, sugars, steroids and synthetic ligands as well as groups that interact with cell membranes, such as lipids, fatty acids, cholesterol, dansyl compounds, and amphotericin derivatives. The signal may increase binding of a compound to the cell surface and/or its association with an intracellular compartment. Other targeting groups can be used to increase the delivery of the polynucleotide to certain parts of the cell, such as nuclear localization signals.

EXAMPLES

Example 1

Reporter Polynucleotides

The pCI-Luc-K expression vector was generated by ligating the CMV enhancer/promoter (pCI mammalian expression vector—Promega, Madison, Wis.) to the expression cassette of the firefly luciferase reporter gene (pSP-luc+ expression vector—Promega) and replacing the ampicillin antibiotic resistance gene with the kanamycin antibiotic resistance gene. pCI-LacZ is similar to pCI-Luc-K and contained the β-galactosidase reporter gene under control of a cytomegalovirus enhancer/promoter. pCMV-hSEAP expresses human secreted alkaline phosphatase, hSEAP, from the cytomegalovirus enhancer/promoter. pMIR59 contains the rat erythropoietin gene under control of the muscle creatine kinase enhancer/promoter. pMIR48 contains the firefly luciferase gene under control of the cytomegalovirus enhancer/promoter. pMIR68 contains the firefly luciferase gene under control of the the ubiquitin C promoter and a hepatic control region for enhancement of long-term expression. pMIR152 contains the murine interleukin 2 under control of the cytomegalovirus promoter. Reporter or marker genes, such as the genes for luciferase and β-galactosidase, serve as useful paradigms for expression of intracellular proteins in general. Similarly, reporter or marker genes, such as secreted alkaline phosphatase (SEAP) serve as useful paradigms for secreted proteins in general. Also, inhibition of reporter gene expression, such as following delivery of siRNA, indicate the reasonable probability of inhibiting other genes by delivering appropriate siRNA.

Example 2

Intravenous Injection into the Small (External) Saphenous Vein Provides Effective Delivery of Polynucleotides to Limb Skeletal Muscle 120-140 g adult Sprague-Dawley rats were anesthetized with 80 mg/kg ketamine and 40 mg/kg xylazine and the surgical field was shaved and prepped with an antiseptic. The animals were placed on a heating pad to prevent loss of body heat during the surgical procedure. A 4 cm long abdominal midline incision was made after which skin flaps were folded away and held with clamps to expose the target area. A moist gauze was applied to prevent excessive drying of internal organs. Intestines were moved to visualize the iliac veins and arteries. Microvessel clips were placed on the external iliac, caudal epigastric, internal iliac, deferent duct, and gluteal arteries and veins as well as on the inferior vena cava near the bifurcation to block both outflow and inflow of the blood to the leg. An efflux enhancer solution (e.g., 0.5 mg papaverine in 3 ml saline) was injected into the small saphenous vein though a 27 g needle. 1-10 minutes later, a 27 G butterfly needle was inserted into the same site and 10.5 ml normal saline containing 500 μg pMIR48 plasmid DNA encoding firefly Luciferase was injected at a rate of 0.583 ml/sec. Fluid was injected in the direction of normal blood flow. The microvessel clips were removed 2 minutes after the injection and bleeding was controlled with pressure and gel foam. The abdominal muscles and skin were closed with 4-0 dexon suture. Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per gram of muscle tissue was determined. The muscle descriptions indicate the following muscle groups of the hindlimb: Quad—anterior muscles of upper leg; Biceps—medial muscles of upper leg; Hamstring—posterior muscles of upper leg; Gastroc—posterior muscles of lower leg; Shin—anterior muscles of lower leg; Foot—muscles of the dorsal foot. Luciferase expression was observed in muscles throughout the limb distal to the occlusion. Highest expression levels were observed near the site of injection.

TABLE 1

Gene delivery to muscles of the leg by intravenous injection of plasmid DNA.
ng Luciferase/g Muscle

| animal | Quad | Biceps | Hamstring | Gastroc | Shin | Foot | total |
|---|---|---|---|---|---|---|---|
| 1 | 664.8 | 402.8 | 98.0 | 237.0 | 359.2 | 0.6 | 360.8 |
| 2 | 1690.1 | 1515.8 | 848.7 | 195.7 | 3471.4 | 4.6 | 1200.4 |
| 3 | 619.5 | 353.3 | 45.5 | 104.6 | 61.8 | 0.3 | 260.0 |
| mean | 991.5 | 757.3 | 330.7 | 179.1 | 1297.5 | 1.8 | 607.1 |
| SEM | 349.6 | 379.5 | 259.4 | 39.1 | 1090.4 | 1.4 | 298.1 |

Example 3

Intravenous Injection Into the Medial Saphenous Vein Provides Effective Delivery of Polynucleotides to Limb Skeletal Muscle In this experiment we performed antegrade injections into the medial saphenous vein. For this injection an abdominal incision and an incision were made along the inside of the hind limb to expose the saphenous vein. Microvessel clips were placed on the external iliac, caudal epigastric, internal iliac, superior vesical, and gluteal arteries and veins as well as on the inferior vena cava near the bifurcation to block both outflow and inflow of the blood to the leg. A pretreatment of papaverine (3.0 ml) was injected by hand into the saphenous vein (antegrade). 5 minutes later, a 27 gauge butterfly catheter was inserted into the saphenous vein and connected to a syringe pump. The 10 ml solution containing 500 μg plasmid DNA (pMIR48) was delivered at a flow rate of 20 ml/min. Swelling throughout the limb was observed after the injection. Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per gram of muscle tissue was determined. Luciferase expression was observed in muscles throughout the limb distal to the occlusion. Highest expression levels were observed near, or just distal to, the vessel occlusion. In this procedure the clamps were positioned close to the biceps.

gram of muscle tissue was determined. Luciferase expression was observed in muscles throughout the limb distal to the occlusion. Highest expression levels were observed in the gastrocnemius and the hamstring muscle. These muscles were close to the site of vessel occlusion and also near the injection site.

TABLE 3

Gene delivery to muscles of the leg by intravenous injection of plasmid DNA.
ng Luciferase/g Muscle

| animal | Quad | Biceps | Hamstring | Gastroc | Shin | Foot | total |
|---|---|---|---|---|---|---|---|
| 1 | 5.5 | 8.0 | 396.0 | 474.0 | 180.3 | 0.5 | 190.0 |
| 2 | 7.7 | 7.9 | 201.0 | 430.4 | 100.3 | 1.0 | 143.4 |
| 3 | 1.3 | 3.0 | 54.5 | 521.0 | 119.4 | 0.3 | 118.7 |
| mean | 4.8 | 6.3 | 217.1 | 475.1 | 133.4 | 0.6 | 150.7 |
| SEM | 1.9 | 1.6 | 98.9 | 26.1 | 24.1 | 0.2 | 20.9 |

Example 5

Delivery of Luciferase DNA Vector to Rat Limb Muscle Cells Via Venous Injection

500 μg of pDNA (pCI-Luc-K) in 3 ml of normal saline solution (NSS) was used for all intravascular and intramuscular DNA injections into ~150 g Sprague-Dawley rats (Harlan Laboratories, Indianapolis, Ind.). Blood flow to and from the limb was restricted just prior to and during the injection, and for 2 min post-injection by placing a tourniquet around the upper leg Oust proximal to/or partially over the quadriceps muscle group). Subsequently 1.5 ml of a papaverine

TABLE 2

Gene delivery to muscles of the leg by intravenous injection of plasmid DNA.

| | Quad | Biceps | Hamstring | Gastroc | Shin | Foot | total |
|---|---|---|---|---|---|---|---|
| Tissue Weight (g) | 1.57 | 1.28 | 1.5 | 1.1 | 0.55 | 0.06 | 6.06 |
| Luciferase RLUs | 7,016,230 | 69,733,530 | 8,775,140 | 14,942,710 | 3,289,150 | 4950 | 103,761,710 |
| Luciferase (ng) | 537 | 5335 | 671 | 1143 | 83.9 | 0.05 | 7770 |
| ng Luciferase/g Muscle | 342 | 4168 | 448 | 1039 | 152 | 0.8 | 1282 |

Example 4

Intravenous Injection Into the Great (Medial) Saphenous Vein Provides Effective Delivery of Polynucleotides to Limb Skeletal Muscle An incision was made extending from the groin to the ankle. A segment of the distal medial saphenous vein was dissected free and a clamp was placed on the distal vein. The proximal femoral vein and artery were also dissected free and clamped as well as the epigastric artery and vein. A pretreatment of papaverine (2.0-2.5 ml) was injected antegrade by hand into the saphenous vein. After 5 minutes, a 27 gauge butterfly needle catheter was inserted into the saphenous vein and connected to a syringe pump. 5.0 ml of plasmid DNA (250 μg) was then injected at a flow rate of 10 ml/min. The lower limb muscles were swollen and some leakage occurred from the injection site as the injection progressed. After 2 minutes the clamps were removed and the vein allowed to reperfuse. Within several minutes the muscle regained a pink color and the vein returned to normal. Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per solution was injected (250 μg papaverine in 1.5 ml NSS) at a distal site in the great saphenous vein. Papaverine was pre-injected to stimulate vasodilation and increases vascular permeability (Budker et al. 1998, Lee et al. 1978). Two minutes after the papaverine injection, pDNA (pCI-Luc-K in normal saline solution) was injected into the great saphenous vein of the distal hind limb at a rate of 3 ml per ~20 seconds (10 ml/min; FIG. 1). The intravenous injections were performed in an anterograde direction (i.e., with the blood flow) via a needle catheter connected to a programmable Harvard PHD 2000 syringe pump (Harvard Instruments). Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per gram of muscle tissue was determined.

Figure 2:
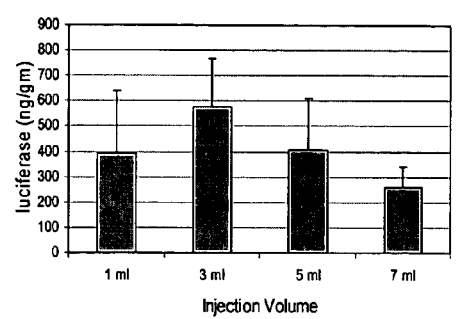
FIG. 2A-2B. Graph illustrating the effects of volume of injection (A) and rate of injection (B) on luciferase expression following intravenous delivery of pDNA (pCI-Luc-K) into the hind limbs of female Sprague-Dawley rats (120-150 g). For each data point, 2 to 7 limbs were injected and analyzed. T-bars indicate standard deviation.
Figure 2:
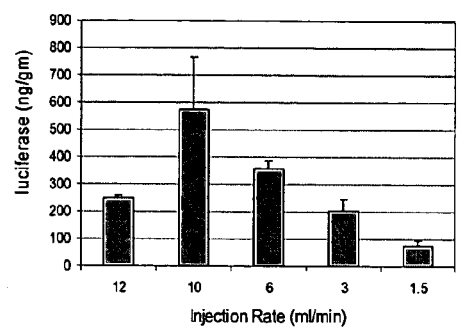

Results—The venous procedure facilitated high level gene delivery to nearly all limb muscle groups distal to blood vessel occlusion (>500 ng luciferase per gram of muscle of lower limb) (FIG. 2 and Table 4). Highest delivery efficiencies were observed using an injection volume of 3 ml (when using 500 μg of pDNA) and an injection rate of between 6 and 12 ml per min. Expression was dose dependent and higher luciferase levels (~1000 ng/g muscle) were achieved by simply increasing the amount of pDNA injected.

TABLE 4

Luciferase expression in individual muscle groups (ng Luciferase/g Muscle).

|  | Quad | Biceps | Hamstring | Gastroc | Shin | Foot | Total |
|---|---|---|---|---|---|---|---|
| Experiment #1 | | | | | | | |
| Rat #1 | 409 | 275 | 685 | 859 | 433 | 5.5 | 548 |
| Rat #2 | 197 | 213 | 729 | 1142 | 244 | 4.5 | 549 |
| Rat #3 | 85 | 312 | 360 | 311 | 76 | 0.3 | 257 |
| Mean ± St. Dev. | 230 ± 165 | 267 ± 50 | 592 ± 202 | 771 ± 422 | 251 ± 179 | 3.4 ± 2.7 | 452 ± 168 |
| Experiment #2 | | | | | | | |
| Rat #1 | 71 | 228 | 745 | 1163 | 307 | 5.6 | 559 |
| Rat #2 | 34 | 378 | 1259 | 1939 | 1226 | 7.8 | 907 |
| Rat #3 | 143 | 191 | 1634 | 468 | 187 | 6.3 | 580 |
| Rat #4 | 425 | 587 | 740 | 936 | 184 | 0.2 | 637 |
| Mean ± St. Dev. | 168 ± 177 | 346 ± 180 | 1095 ± 435 | 1127 ± 614 | 476 ± 503 | 5.0 ± 3.3 | 671 ± 161 |

Data represents results from 2 different experiments performed on different days (Expt. 1, n=3; Expt. 2, n=4). The muscle descriptions indicate the following muscle groups of the hindlimb: Quad—anterior muscles of upper leg; Biceps—medial muscles of upper leg; Hamstring—posterior muscles of upper leg; Gastroc—posterior muscles of lower leg; Shin—anterior muscles of lower leg; Foot—muscles of the dorsal foot.

Example 6

Comparison of Efficacy for Various Gene Delivery Methods

To compare the levels of in vivo gene expression in limb cells following the venous delivery procedure to that of other commonly used in vivo delivery procedures and vectors, we assayed for transgene expression levels (luciferase) following the administration of a CMV-luciferase adenoviral vector and naked pDNA using other administration routes (Table 5).

Intravenous adenoviral injections—For adenoviral vector injections, $2 \times 10^9$ infectious particles (Ad5CMVLuciferase, University of Iowa Vector Core Facility) were injected in 5 mls of NSS at a rate of 12.5 ml/min. Adenoviral injections were performed into the great saphenous vein as described as for pDNA.

Intra-arterial injections of pDNA—Intra-arterial (iliac) injections were performed as previously described (Budker et al. 1998) with the following modifications, a 10 ml total volume containing 500 µg pCI-Luc-K was injected in 20 sec. For intra-arterial injections, the entire volume was delivered via catheter connected to a Harvard PHD2000 syringe pump.

Intramuscular injections—For direct intramuscular injections, a total volume of 3 ml ($2 \times 10^9$ infectious particles adenovirus in NSS or 500 µg pCI-Luc-K pDNA in NSS) was used to mimic the increase in limb volume following the intravascular injections. The 3 ml volume was split and injected (by hand) proportionately into the gastrocnemius, quadriceps, biceps, hamstring and shin muscle groups. All muscles were harvested at 5 days post-injection and assayed for luciferase activity.

TABLE 5

Comparison of muscle expression following delivery of pDNA or adenovirus vectors into hind limb muscle of rats (n = 2 – 7).

| Vector | Route of Administration | Injection Volume | Injection Rate (ml/min) | Luciferase Levels (ng/g of muscle) |
|---|---|---|---|---|
| pCI-Luc-K | Intravenous | 3 ml | 10 | 577 ± 190 |
|  | Intra-arterial | 10 ml | 20 | 480 ± 285 |
|  | Intramuscular | 3 ml | ~10 | 19.9 ± 11.7 |
| Ad5-CMVLuc | Intravenous | 5 ml | 12.5 | 7.0 ± 5.3 |
|  | Intramuscular | 3 ml | ~10 | 0.1 ± 0.02 |

The intravenous injection of naked pDNA enabled approximately 80-times more luciferase expression than the intravenous injection of the adenoviral vector. Intravenous delivery of pDNA was also more efficient than direct intramuscular injection of pDNA (~30-fold higher transgene expression) and comparable to the expression levels achievable with intra-arterial delivery (Table 5). To obtain similar levels of gene delivery (pDNA) using the arterial procedure, a significantly higher volume and rate of injection was required (Table 5). Also of significant interest, IV injection of Adenovirus, using injection volume and injection rate similar to that used for naked DNA delivery, resulted in much greater (70-fold) effective gene delivery to muscle cells than direct injection of Adenovirus.

Example 7

Determination of Percentage of Transfected Myofibers

Intravenous injections of pCI-LacZ plasmid DNA were performed into the distal limbs of rats (great saphenous vein). For β-galactosidase staining, samples were taken from each muscle group, frozen in cold isopentane and stored at −80° C. 10 µm thick cryostat sections were cut from portions of the proximal, middle and distal locations of each muscle group. The sections were fixed and incubated in an X-gal staining solution (Mirus Corporation, Madison, Wis.) for one hour at 37° C. To maximize visualization of the blue cells (i.e., β-galactosidase positive), gastrocnemius sections (A) were not counterstained. All shin muscle sections were counter stained with hematoxylin (B). The muscle tissue not used for sectioning was weighed and analyzed by a chemiluminescent assay for β-galactosidase (Galactolight, Applied Biosystems, Bedford, Mass.). To minimize immune effects related to expression of the foreign protein (β-galactosidase) all rats were immunosuppressed. Animals received both FK-506 (2.5 mg/kg. PO) and dexamethasone (1 mg/kg, IM) one day before injection, one hour before injection and one day after injection. Animals then continued to receive FK506 (2.5 mg/kg, PO) everyday throughout the study.

Figure 3:
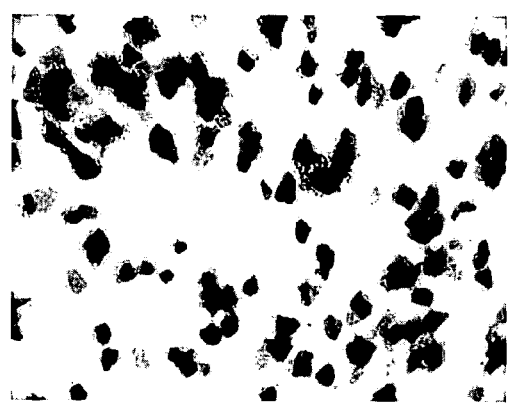
FIG. 3. Photomicrographs of rat limb gastrocnemius muscle stained for β-galactosidase following single intravenous injections of 500 μg of pDNA (pCI-LacZ).

After a single intravenous injection of 500 µg of pCI-LacZ (in 3 ml NSS over 20 s), β-galactosidase expression was detected in all muscle groups (range of 3-45% β-galactosidase positive cells) of the lower limb distal to the tourniquet (FIG. 3). One of the highest expressing muscle groups was the gastrocnemius in which approximately 30-45% of cells stained positive for the transgene in high expressing areas of the muscle (FIG. 3). Chemiluminescence determination of β-galactosidase expression gave 20,917,900 RLUs in the gastrocnemius muscle and 1,158,200 RLUs in the shin muscle.

Example 8

Multiple (Repeat) Injections

Figure 4:
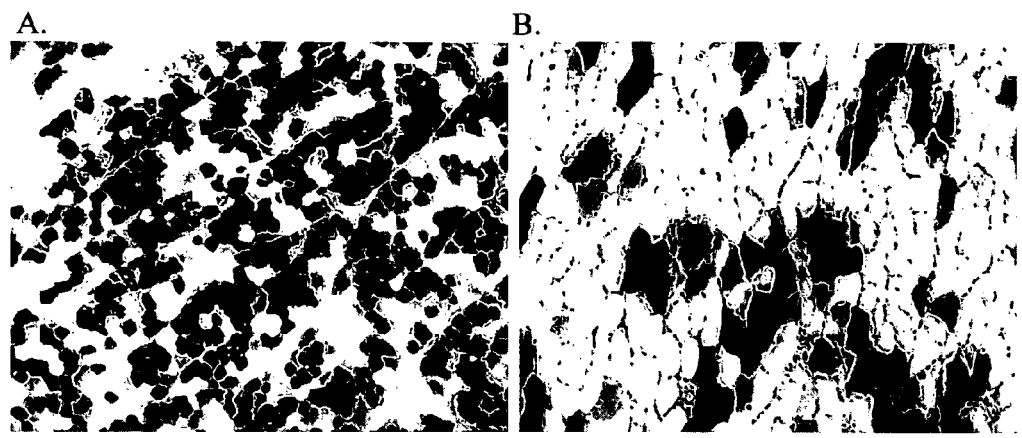
FIG. 4. Photomicrographs of rat limb gastrocnemius (A) and shin (B) muscles stained for β-galactosidase following repeat (triple) intravenous injections of 500 μg of pDNA (pCI-LacZ).

A Sprague-Dawley rat was injected intravenously three-times with 500 µg of pCI-LacZ on days 0, 4, and 8 and muscles were harvested on day 10. Injections were performed, via catheterization, on days 0, 4, and 8 at different sites: lateral plantar vein, small saphenous, and great saphenous respectively. For each injection, all volumes and amounts injected were as described as above. β-galactosidase staining was performed as described above. Additional injections resulted in significantly higher percentages of cells expressing the transgene (FIG. 4). In the gastrocnemius of the rat limb that was thrice injected, β-galactosidase expression was observed in about 60-80% of the cells in high-expressing areas (FIG. 4). β-galactosidase enzyme assays on the individual muscle groups correlated the histochemical analyses, 52,959,500 RLUs in the gastrocnemius muscle and 11,894,700 RLUs in the shin muscle.

Example 9

Intravenous Delivery of a Gene Encoding a Secreted Protein

To determine if intravenous gene delivery to muscle could be used to deliver a secreted protein into the bloodstream, single and repeat intravenous injections of pCMV-hSEAP were performed using a secreted reporter gene expression construct. At day 8 post-injection, rats injected once (at day 0, as describe above) had mean serum hSEAP concentrations of 374 ng/ml (±264, n=3), while rats that received 2 injections (at days 0 and 5) had mean concentrations of 631.6 ng/ml (±156, n=5).

Figure 5:
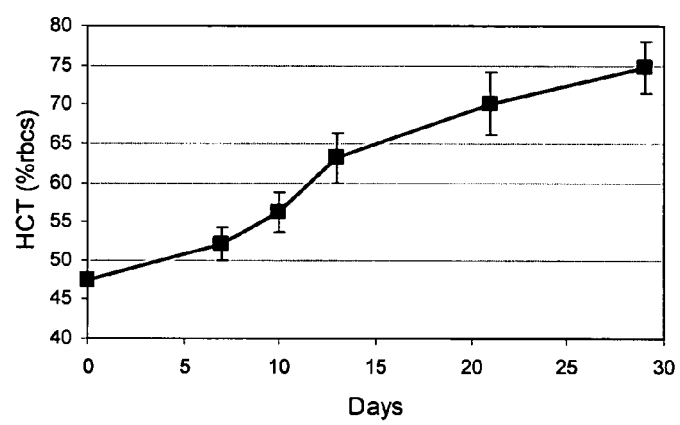
FIG. 5. Intravascular injection of therapeutic genes into mammalian limbs. Time course of erythropoietin expression following injection of 500 μg pDNA (in 3 ml NSS/20 s) encoding rat erythropoietin into great saphenous vein of distal limb of 120-150 g female Sprague-Dawley rats (n=3).

Rats injected with a polynucleotide (pMIR59, injections as described above) encoding the therapeutically relevant erythropoietin, had their hematocrits increase continuously from a baseline of 47% to ~75% within the first 29 days (FIG. 5).

Example 10

Intravenous Delivery of the Therapeutically Relevant Dystrophin Gene to Limb Muscle Cells in Mouse A clinically-relevant example is provided by the intravenous delivery of the human dystrophin gene into the mdx4cv mouse model for Duchenne muscular dystrophy, the dystrophin-negative strain B6Ros.Cg-DMD$^{mdx-4Cv}$ (Jackson laboratory). For each injection, 300 µg of a pDNA human dystrophin expression vector (Acsadi et al. 1991) in 0.6 ml of NSS (7.5 s injection) was injected into a distal site in the great saphenous vein of the mouse hindlimb. Fluid flow into and out of the leg was occluded by means of a tourniquet. Blood flow was occluded prior to injection and for two minutes following the injection. Immunohistochemical staining for human dystrophin expression in mdx4cv mouse muscle (from gastrocnemius) was performed one week post-injection using a mouse, anti-dystrophin polyclonal primary antibody and a FITC-conjugated goat, anti-mouse IgG (FAB specific; Sigma) secondary antibody. Similar percentages of dystrophin-positive myofibers were detected using a monoclonal antibody specific for human dystrophin (NCL-DYS3, Novocastra Laboratories). Images were captured using a 10× objective (Zeiss Axioplan 2 fluorescent microscope).

Figure 6:
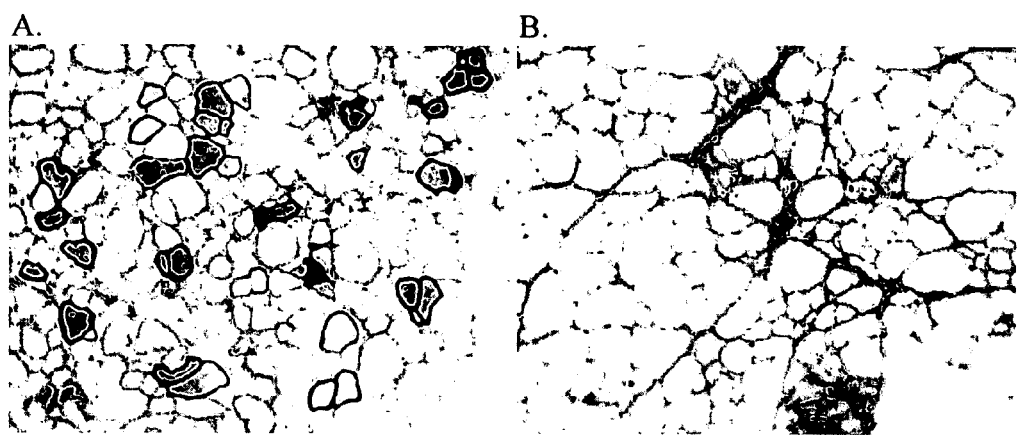
FIG. 6. Intravascular injection of therapeutic genes into mammalian limbs. Immunohistochemical staining for human dystrophin expression in mdx4cv mouse gastrocnemius muscle (left panel) one week after intravenous injection of 300 μg of a pDNA human dystrophin expression vector in 0.6 ml of NSS (7.5 s injection). Staining in mdx4cv mice injected with pCI-Luc negative control vector is shown in the right panel.

In four mdx4cv mice injected once intravenously with a plasmid expression vector encoding full-length, human dystrophin, 3-15% of myofibers of various hindlimb muscles exhibited sarcolemmal dystrophin expression (FIG. 6). Dystrophin-positive revertants in this particular mdx strain are below 0.5% (FIG. 6). The ability to perform the intravenous procedure in mouse models enhances its utility as a research tool.

Example 11

Intravenous Delivery of Polynucleotides to Limb Muscle Cells in Dog 9.5 kg beagles were induced with acepromazine (0.1 mg/kg, SQ) and morphine (1.5 mg/kg, IM) followed 10-20 minutes later by thiopental (10-15 mg/kg, IV). Animals were then intubated, connected to an anesthesia machine and maintained with 1 to 2% isoflurane. A front limb to be injected was shaved and a modified pediatric blood pressure cuff was attached just above the elbow. A 20 gauge intravenous catheter (length=1.8 inches) was inserted into the distal cephalic vein and secured with tape. Blood samples were collected for a complete blood count (CBC) and chemistry panel. The catheter was then connected to a three-way stopcock and flushed with ~2 ml saline to remove any blood in the catheter. After inflating the blood pressure cuff to a pressure greater than 300 mmHg to impede fluid flow to and from the limb, a 25 ml NSS containing 4.2 mg papaverine (Sigma, St Louis, Mo.) and 150 units of heparin was injected by hand over 10 seconds. For the pDNA injection, the three-way stopcock was connected to two PHD 2000 syringe pumps each loaded with a single syringe. Five minutes after the papaverine injection, 20 mg of pCI-Luc-K in 36-40 ml NSS was injected at a rate of 2 ml per second. Two minutes after the polynucleotide injection, the blood pressure cuff was released and the catheter was removed. Animals were given analgesics (buprenorphine, 0.01 to 0.02 mg/kg, IM) once at the time of the injection and again after the procedure. The left front limb was injected on day 0 and the right front limb was injected on day 3. Blood samples were collected just before each injection, one day after each injection and just before sacrifice on day 7. After recovering from anesthesia, animals were able to move around freely using the injected limb. 24 hours after injection there was no sign of swelling in the injected limb.

TABLE 6

Luciferase expression in dog (beagle) forelimb muscle cells following in vivo IV delivery of plasmid encoding the luciferase gene.

| Limb | Injection Site | Volume (ml) | pDNA (mgs) | Rate (ml/sec) | Total Luciferase per Leg (ng/g) |
|---|---|---|---|---|---|
| front (right) | cephalic vein | 40 | 20 | 2.0 | 93 (day 4) |
| front (left) | cephalic vein | 36 | 20 | 2.0 | 419 (day 7) |

TABLE 7

Luciferase activity in dog forelimb muscle cells following in vivo IV delivery of plasmid encoding the luciferase gene.

| Muscle group | Muscle name | 4 day | 7 day |
|---|---|---|---|
| Dorsolateral antebrachial muscles | Extensor carpi radialis | 135.6 | 2297.8 |
| | Extensor digitorum communis | 552.1 | 421.1 |
| | Extensor digitorum lateralis | 77.9 | 488.7 |
| | Extensor carpi ulnaris | 22.9 | 22.4 |
| | Extensor pollicis longus et indicis proprius | 222.8 | 60.8 |
| | Supinator | 262.6 | 182.6 |
| Caudal antebrachial muscles | Flexor carpi radialis | 14.3 | 294.7 |
| | Flexor carpi ulnaris | 3.5 | 14.4 |
| | Flexor digitorum superficialis | 49.1 | 47.6 |
| | Flexor digitorum profundus | 55.5 | 160.8 |
| | Pronator teres | 35.5 | 333.7 |
| | Pronator quadratus | 260.7 | 230.2 |
| Muscles of forepaw | Muscles of forepaw | 89.2 | 123.6 |
| | Weighted average: | 92.6 | 419.1 | ng Luciferase/g muscle

A weighted average was calculated by dividing the total luciferase expressed (in nanograms) by the total weight of the limb muscles analyzed (in grams).

Example 12

Intravenous Delivery of Polynucleotides Into Primate (Rhesus Monkey)

Three adult rhesus primates were used in this study. Primate #1 was a 8.8 kg male, primate #2 was a 6.0 kg female and primate #3 was a 4.2 kg male. Animals were induced with ketamine (15 mg/kg, IM), intubated and anesthesia maintained with 1-2% isoflurane. The limb to be injected was shaved and a modified pediatric blood pressure cuff (sphygmomanometer) was attached just proximal the elbow (or knee). A 22 gauge intravenous catheter (length=1.0 inches) was inserted into the selected vein (great saphenous, small saphenous, cephalic or median vein) and secured with tape. Blood samples were collected for a complete blood count (CBC) and chemistry panel. The catheter was then connected to a three-way stopcock and flushed with saline. After inflating the blood pressure cuff to a pressure greater than 300 mmHg, to block inflow and outflow of blood in the distal limb (FIG. 1B), a 20-30 ml saline solution containing 5 mg of papaverine and 150 Units of heparin was injected by hand over 10 seconds. For the pDNA injection, the three-way stopcock was connected to two syringe pumps each loaded with a single syringe. 5 min after the papaverine injection, pDNA (15.5-25.7 mg in 40-100 ml NSS) was injected at a rate of 1.7 or 2.0 ml per second. Two minutes after the pDNA injection, the blood pressure cuff was released and the catheter was removed. Animals were given analgesics (buprenorphine, 0.01 mg/kg, IM) once at the time of the injection and again after the procedure.

Primate #1 had the left forearm (16.5 mg pCI-Luc) and right hind limb (21.3 mg pCI-Luc) injected on day 0 and the right forearm (15.5 mg pCI-Luc) and left hind limb (25.7 mg pCI-Luc) injected on day 3. Primate #2 had the left forearm (20 mg pCI-Luc-K) and the right hind limb injected (20 mg pCI-LacZ) on day 0 and the right forearm (20 mg pCI-Luc-K) and the left hind limb injected (20 mg pCI-LacZ) on day 3. Primate #3 had the left forearm (20 mg pCI-Luc-K) and right hind limb (40 mg pCI-LacZ) injected on day 0 and the right forearm (plasmids plus siRNA) and left hind limb (plasmids plus siRNA) injected on day 3. Blood samples were collected just before injection, one day after injection and just before sacrifice on day 7. After recovering from anesthesia, the animals were able to move around freely using the injected limbs. Twenty four hours after injection there was only minor swelling and small areas of bruising in the injected limb.

Animals were euthanized on the indicated days and luciferase assays, muscle sectioning, hemotoxylin counterstaining and β-galactosidase staining were performed as described for rat studies. Photomicrographs were captured using a 10× or 20× objective (Zeiss Axioplan 2 microscope). Percent β-galactosidase positive cells were quantitated by dividing the total number of blue stained cells by the total number of myofibers on a given section and multiplying by 100.

TABLE 8

Luciferase expression in rhesus monkey limb muscle cells following in vivo IV delivery of plasmid encoding the luciferase gene.

| Animal | Limb | Injection Site | Volume (ml) | pDNA (mgs) | Rate (ml/sec) | Total Luciferase per leg (ng/g) |
|---|---|---|---|---|---|---|
| 1 | arm | cephalic vein | 100 | 16.5 | 1.7 | 513 (day 7) |
| 1 | leg | small saphenous vein | 100 | 21.3 | 1.7 | 543 (day 7) |
| 1 | arm | cephalic vein | 70 | 19.8 | 2.0 | 215 (day 4) |
| 1 | leg | great saphenous vein | 90 | 19.8 | 2.0 | 464 (day 4) |
| 2 | arm | cephalic vein | 40 | 20 | 2.0 | 386 (day 7) |
| 2 | arm | median vein | 40 | 20 | 2.0 | 98.2 (day 4) |

TABLE 9

Luciferase expression in rhesus monkey arm muscle cells following in vivo IV delivery of plasmid encoding the luciferase gene

| | | ng Luciferase/g muscle | | | |
|---|---|---|---|---|---|
| | | Primate #1 | | Primate #2 | |
| Muscle group | Muscle name | Day 4 | Day 7 | Day 4 | Day 7 |
| Anterior group | | | | | |
| Superficial group | Palmaris longus | 52.0 | 317.7 | 6.2 | 74.4 |
| | Pronator teres | 27.8 | 85.3 | 268.9 | 266.6 |
| | Flexor carpi radialis | 330.2 | 497.4 | 846.3 | 1322.1 |
| | Flexor carpi ulnaris | 32.0 | 26.8 | 20.9 | 566.0 |
| | Flexor digitorum spf. | 54.2 | 102.3 | 3.3 | 54.2 |
| Deep group | Flexor digitorum prof. | 108.5 | 177.4 | 11.6 | 156.7 |
| | Pronator quadratus | 525.3 | 250.1 | 54.3 | 188.4 |
| Posterior group | | | | | |
| Superficial group | Brachioradialis | 242.5 | 1507.8 | 165.6 | 1439.8 |
| | Extensor carpi radialis longus | 144.4 | 1251.6 | 2.3 | 25.9 |
| | Extensor carpi radialis brevis | 99.1 | 776.5 | 32.8 | 78.9 |
| | Extensor digitorum | 1316.8 | 1229.6 | 28.8 | 343.8 |
| | Anconeus | 286.4 | 156.9 | 29.3 | 336.8 |
| | Extensor carpi ulnaris | 258.2 | 748.9 | 5.4 | 29.4 |
| | Extensor pollicis longus | 251.5 | 90.9 | 5.6 | 106.7 |
| Deep group | Supinator | 553.3 | 584.4 | 80.6 | 640.9 |
| | Abductor pollicis longus | 327.5 | 261.4 | 26.5 | 354.4 |
| | Extensor digiti secund et teriti | 385.5 | 379.2 | na* | na |
| | Extensor digiti quart et minimi | 336.8 | 314.0 | 11.1 | 111.7 |
| Muscles of the hand | Thumb muscles | 455.4 | 1047.5 | 30.6 | 180.2 |
| | Interosseus | 598.0 | 1365.8 | 202.5 | 837.3 |
| | Others | 525.6 | 55.7 | 11.6 | 61.4 |
| | Weighted average: | 215.0 | 542.1 | 98.2 | 385.9 | na = not asssayed

TABLE 10

Luciferase expression (ng/g muscle) in Rhesus Macaque Leg Muscles

| | ng Luciferase/g muscle | |
|---|---|---|
| Muscle name | Day 4 (ng/g) | Day 7 (ng/g) |
| Gastrocnemius | 455.2 | 261.2 |
| Soleus | 1464.3 | 1038.9 |
| Popliteus | 2442.4 | 452.5 |
| Flexor digitorum longus | 75.4 | 985.9 |
| Flexor hallucis longus | 117.2 | 555.8 |
| Tibialis posterior | 400.5 | 788.5 |
| Tibialis anterior | 266.1 | 222.4 |
| Extensor hallucis longus | 197.9 | 377.0 |
| Extensor digitorum longus | 969.0 | 1994.7 |
| Abductor hallucis longus | 61.3 | 85.6 |
| Peronaus longus | 207.6 | 824.4 |
| Peronaus brevis | 59.2 | 733.7 |
| Extensor digitorum brevis | 1.6 | 6.4 |
| Extensor hallucis brevis | 10.3 | 123.7 |
| Other foot muscles | 4.7 | 123.0 |
| Weighted average: | 464.5 | 513.4 |

A weighted average was calculated by dividing the total luciferase expressed (in nanograms) by the total weight of the limb muscles analyzed (in grams).

Figure 7:
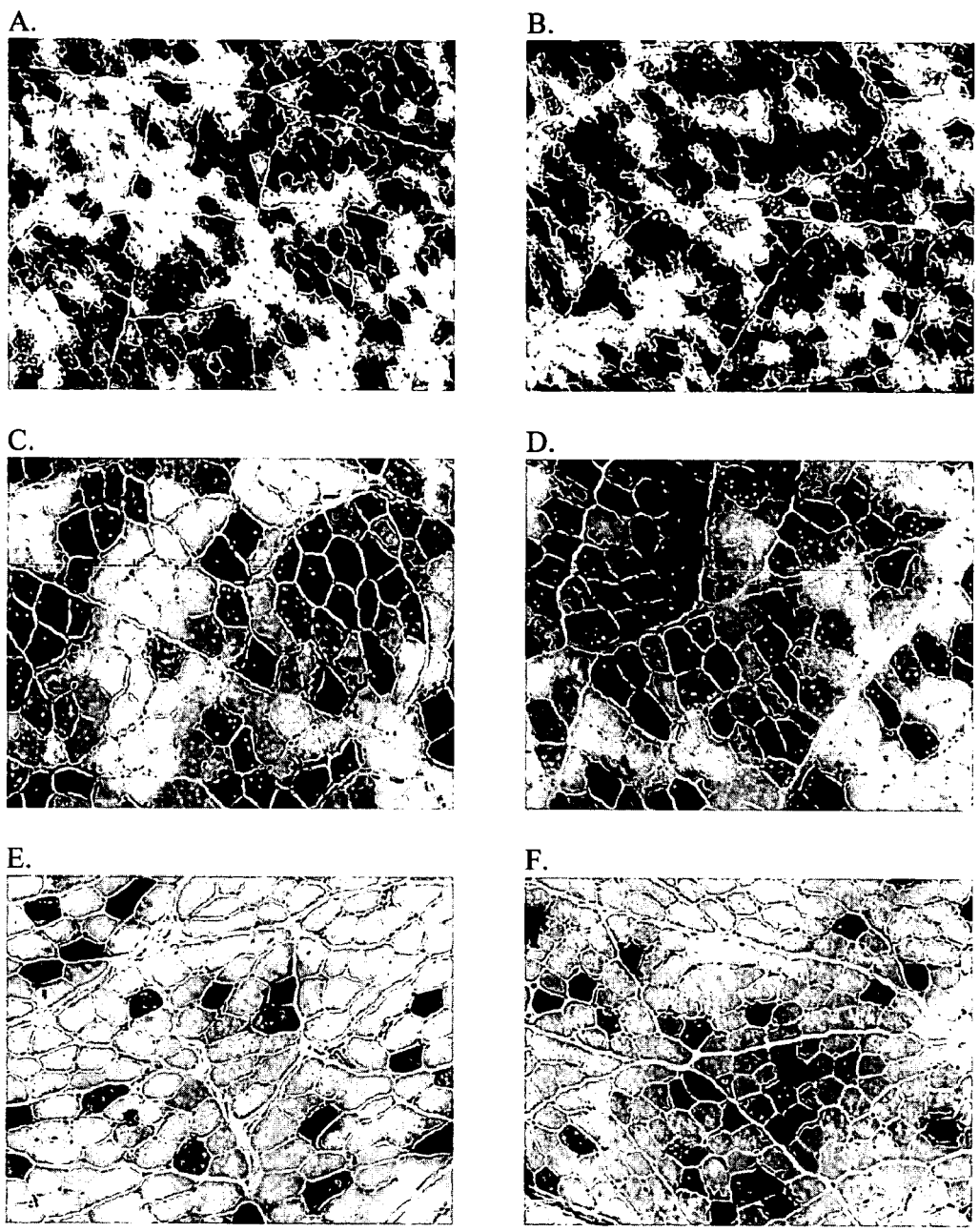
FIG. 7A-7F. Photomicrographs from three different lower limb muscle groups stained for β-galactosidase following a single intravenous injection of 40 mg of pDNA (pCI-LacZ) into a distal site of the great saphenous vein. (A-B) gastrocnemius muscle, (C-D) soleus muscle, (E-F) extensor hallucis brevis. Individual panels indicate representative high-expressing areas in two different locations of each muscle group.

Intravenous injections with pCI-LacZ and subsequent β-galactosidase histochemical analyses indicate that myofibers were transfected in primates as in rats. In the hind limb of primate #2 injected with pDNA encoding β-galactosidase, expression was observed in all muscle groups of the lower limbs. The percentage of transfected myofibers in high expressing areas of three targeted muscle groups (gastrocnemius, soleus, extensor hallucis brevis) ranged from 11% to 49% (FIG. 7). For two of the targeted distal limb muscle groups (soleus muscle, small muscles of the foot) a more quantitative analysis was performed by counting β-galactosidase positive cells from multiple sections chosen randomly throughout the muscle group. Using this analysis technique, the soleus muscle showed an overall transfection efficiency of 25.4% (2453 lacZ positive cells/9650 total cells counted) while the small muscles of the foot displayed an overall transfection efficiency of 7.3% (205 lacZ positive cells/2805 total cells counted).

Example 13

Intravenous Delivery of SiRNAs Into Rat and Primate Limb Muscle Cells

Figure 8:
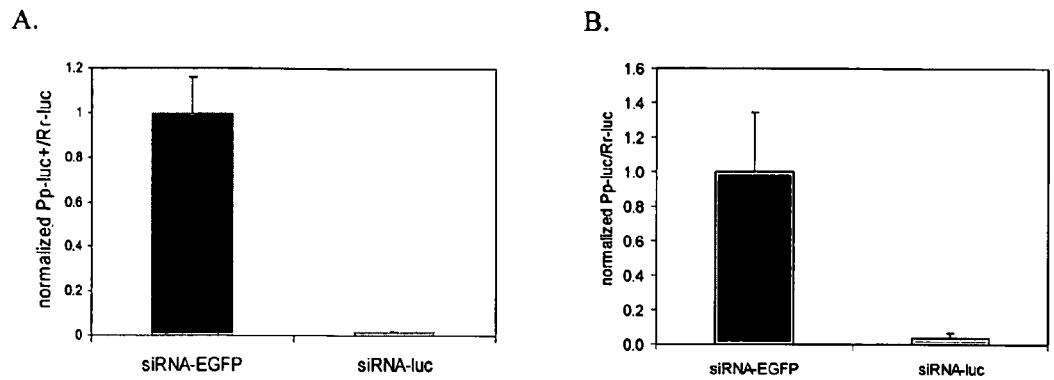
FIG. 8. RNA interference in rat and primate limb muscle following intravenous co-delivery of siRNAs and pDNA expression vectors. Firefly luciferase knockdown in limb muscle using the targeted siRNA was plotted against firefly luciferase knockdown using the control siRNA (EGFP) that was normalized to 1. (5A) rat, (5B) monkey.

Intravenous injection can also be used for delivering other macromolecules into muscle tissue. RNA interference is a recently recognized phenomenon in which target gene expression (in mammalian cells) can be selectively inhibited following the introduction of double stranded RNA into a cell (Elbashir et al. 2001). However, achieving effective gene knockdown in vivo (via RNA interference) requires efficient delivery of a polynucleotide (21-23 bp double stranded RNAs; termed siRNA or microRNA) into the target cells. To delivery siRNA to extravascular limb cells to achieve RNA interference in myofibers in vivo, siRNAs (targeted against firefly luciferase) were co-injected with pDNA encoding firefly luciferase (pCI-Luc-K) into the great saphenous vein of C57B1/6 mice, Sprague-Dawley rats and a rhesus macaque. At 2 days post-injection, greater than 95% inhibition of the targeted gene was achieved in the limbs that received the siRNA encoding the firefly luciferase in all three species (FIG. 8).

For delivery of siRNA to rat limb muscle cells, 150 g Sprague Dawley rats were co-injected into the great saphenous vein with 250 µg of a pDNA encoding firefly luciferase (pSP-luc+, Promega) and 25 µg of a pDNA (pRL-SV40, Promega) encoding *Renilla reniformis* luciferase. Injections were performed using 3 mls injection volume as described above. One group of animals (n=5) received plasmids alone, one group (n=5) received plasmids plus 12.5 µg of a siRNA targeted against firefly luciferase (siRNA-luc+) and a control group (n=5) received plasmids plus 12.5 µg of a siRNA targeted against enhanced green fluorescent protein (siRNA-EGFP, Clontech). Muscle was harvested 72 hours after injection.

|  | Muscle Group | | | | | |
| --- | --- | --- | --- | --- | --- | --- |
|  | quad | biceps | hamstring | gastroc | shin | total |
| no siRNA | | | | | | |
| average firefly luciferase expression | 2,331,015 | 2,197,626 | 5,701,719 | 6,368,653 | 648,859 | 17,247,871 |
| average *Renilla* luciferase expression | 102,322 | 98,349 | 242,450 | 319,224 | 31,129 | 793,474 |
| average ratio (firefly/*Renilla*) | 23.4 ± 4.5 | 22.3 ± 4.0 | 23.8 ± 3.4 | 22.2 ± 4.7 | 21.3 ± 1.7 | 22.8 ± 3.1 |
| control siRNA | | | | | | |
| average firefly luciferase expression | 692,220 | 2,317,722 | 4,767,100 | 5,296,748 | 514,189 | 12,425,792 |
| average *Renilla* luciferase expression | 25,566 | 105,572 | 188,049 | 252,630 | 24,196 | 540,647 |
| average ratio (firefly/*Renilla*) | 25.6 ± 6.5 | 24.1 ± 3.7 | 26.3 ± 5.2 | 22.2 ± 3.5 | 21.3 ± 0.9 | 24.3 ± 3.9 |
| siRNA | | | | | | |
| average firefly luciferase expression | 44,754 | 103,421 | 105,719 | 223,126 | 54,779 | 531,799 |
| average *Renilla* luciferase expression | 115,517 | 292,509 | 300,648 | 521,484 | 104,106 | 1,334,265 |
| average ratio (firefly/*Renilla*) | 0.46 ± 0.20 | 0.37 ± 0.04 | 0.35 ± 0.05 | 0.44 ± 0.04 | 0.49 ± 0.09 | 0.40 ± 0.03 |

Expression levels were measured by preparing homogenates and measuring activity of the firefly luciferase and the renilla luciferase using the dual luciferase assay kit (Promega). The mean expression levels (from all harvested muscle groups) in animals receiving the siRNA targeted against firefly luciferase was normalized to those animals receiving the control siRNA (EGFP). Animal receiving siRNA against firefly luciferase showed ~60 fold reduction in firefly luciferase expression relative to *Renilla* luciferase expression.

For delivery of siRNA to primate limb muscle cells, injection parameters were used as described above for plasmid delivery studies. One front limb of a rhesus macaque was injected via the cephalic vein with 40 ml of saline containing 10 mg of a pDNA encoding firefly luciferase (pCI-Luc-K), 2.2 mg of a pCMV-Renilla encoding *Renilla reniformis* (sea pansy) luciferase and 750 µg of a siRNA targeted against firefly luciferase (siRNA-luc+). The opposite lower hind limb was injected on the same day via the great saphenous vein with 50 ml of saline containing the same plasmids plus 750 µg of a siRNA targeted against enhanced green fluorescent protein (siRNA-EGFP). 96 hours after injection, animals were euthanized and muscles were harvested. Expression levels were measured with the same technique described in the rat studies. Data was normalized to values obtained for the control siRNA (EGFP). Co-delivery of a plasmid containing an expressible reporter gene was used as a convenient method to quantitatively assay delivery of the siRNA. The invention does not require co-delivery of a plasmid for delivery of siRNA and absence of plasmid DNA in the injection solution will not effect siRNA delivery. For all muscle groups of the forearm (palmaris longus, pronator teres, flexor carpi radialis, flexor carpi ulnaris, flexor digitorum superficialis, flexor digitorum profundus, pronator quadratus, brachioradialis, extensor carpi radialis longus, extensor carpi radialis brevis, extensor digitorum, anconeus, extensor carpi ulnaris, supinator, abductor pollicis longus, ext. digiti secund et teriti, extensor digiti quart et minimi, muscles of the thumb, interosseus, other, muscles of the hand), the ratio of firefly luciferase espression to Renilla luciferase expression was 0.019±0.015.

For all muscle groups of the lower hind limb (gastrocnemius medial, gastrocnemius lateral, soleus, popliteus, flexor digitorum longus, flexor hallucis longus, tibialis posterior, tibialis anterior, extensor hallucis longus, extensor digitorum longus, abductor hallucis longus, peronaus longus, peronaus brevis, extensor digitorum brevis, extensor hallucis brevis, other muscles of the foot), the ratio of firefly luciferase espression to Renilla luciferase expression was 0.448±0.155. Muscles receiving the firefly specific siRNA showed 23.6 fold lower expression of firefly luciferase relative to *Renilla* luciferase.

Example 14

Toxicity Assessment Following Intravenous Delivery of Polynucleotides

All mice, rats, dogs and primates tolerated the procedure well and began using the injected limbs as soon as they recovered from anesthesia. Serum chemistry panels on the injected primates indicated that electrolytes, serum minerals, serum lipids, serum proteins (bilirubin, total protein) were not adversely affected by the injections. Serum liver enzymes (alanine aminotransferase—ALT and aspartate aminotransferase—AST) were slightly elevated (just above the normal range) 1 day after injection and in all cases they returned to the normal range by 48 hours post-injection. A complete blood count (CBC) on the 3 injected primates revealed that overall levels of red blood cells (RBCs) and white blood cells (WBCs) remained in the normal range following the injections. In two of the rhesus macaques a slight elevation of platelets was observed at 7 days post-injection.

Figure 9:
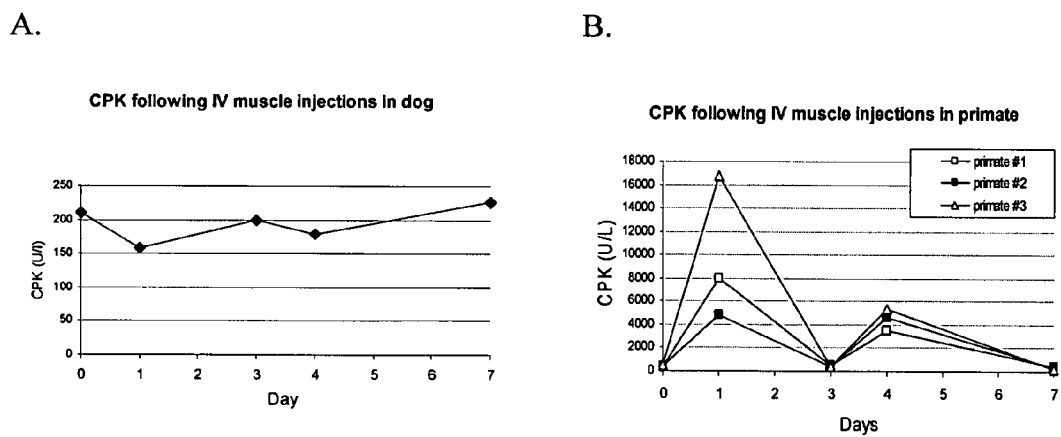
FIG. 9. Time course of creatine phosphokinase (CPK) values following two intravenous injections in beagle (A) and rhesus macaques (B).

To evaluate muscle damage related to the procedure, serum levels of the muscle protein creatine phosphokinase (CPK) were measured in each of the species at various times after injection. In rats injected with 500 µg of pCI-Luc under optimal conditions (in 3 ml normal saline over 20 sec), CPK values showed no substantial changes following injections. In the dog, two sequential intravenous injections in separate legs were performed (at days 0 and 3; 40 ml/leg per injection) and CPK values also showed no substantial changes following the injections (FIG. 9). Normal baseline CPK values in dog and primate range from 16-413 U/L and 0-611 U/L blood respectively. In rhesus monkeys that received injections in two different limbs (arm and leg) on the same day, serum CPK values exhibited transient elevations but returned to baseline levels within several days (FIG. 9). In the monkeys, intravenous injections were done in each animal (into one arm and leg) on day 0 and the contralateral arm and leg on day 3 (i.e., two injections at day 0 and two injections at day 3). The day 3 blood sample (for CPK analysis) in both species was collected prior to the second intravenous injections. The lower CPK values following the second injections may reflect the reduced injection volumes (70-90 ml injected). It is important to note that these transient elevations of CPK levels in monkeys represent minimal amounts of muscle damage. CPK levels of this magnitude accompany various eccentric exercise regimens in normal subjects (Noakes et al. 1987, Nosaka et al. 1996). Studies in human and non-human primates have demonstrated that transient increases in plasma membrane permeability can occur following tourniquet placement onto limbs and following rapid injection of solutions into the vascular system (Chiu et al. 1976, Chetverikova 1977, Modig et al. 1978, Rupinski et al. 1989, Zhang et al. 2004).

Consistent with the CPK data, muscle histology (H&E staining) indicated that minimal necrosis (<0.2% of the myofibers) occurred in rat or rhesus muscle following intravenous injection and that muscle tissue was indistinguishable from non-injected muscle by 7 days post-injection. Maybe most importantly, vein histology (H&E staining) and radiologic venograms (drainage of contrast material) indicated that there was no detectable vascular damage to the veins following injection.

Example 15

Induction of Immune Response in Mice Following Intravenous Delivery of a Polynucleotide Four mice were injected on days 0, 14 and 21 with a plasmid encoding the firefly luciferase gene under control of the cytomegalovirus promoter (pMIR48). For each injection, a solution containing the plasmid was inserted into lumen of the saphenous vein animals as follows: A latex tourniquet was wrapped around the upper hind limb just above the quadriceps and tightened into place with a hemostat to block blood flow to and from the leg. A small incision was made to expose the distal portion of the great (or medial) saphenous vein. A 30 gauge needle catheter was inserted into the distal vein and advanced so that the tip of the needle was positioned just above the knee in an antegrade orientation. A syringe pump was used to inject an efflux enhancer solution (42 µg papaverine in 0.25 ml saline) at a flow rate of 4.5 ml/min followed 1-5 min later by injection of 1.0 ml saline containing 50 µg pDNA at a flow rate of 4.5 ml/min. The solution was injected in the direction of normal blood flow through the vein. Two minutes after injection, the tourniquet was removed and bleeding was controlled with pressure and a hemostatic sponge. The incision was closed with 4-0 Vicryl suture. The procedure was completed in ~10 min.

As controls, two mice were immunized via plasmid delivery to the liver using tail vein injections. Mice received injections on the same day as indicated above. For the tail vein injections, 50 µg plasmid DNA in 2.5 ml Ringer's solution was injected into the tail vein using a 27 gauge needle. The entire volume was delivered in less than 10 sec (U.S. Pat. No. 6,627,616).

To monitor induction of an immune reaction to luciferase, the animals were bled on days—1, 7, 20 and 34. The blood was allowed to clot and the sample was centrifuged to recover the sera. Sera were analyzed for the presence of antibodies to luciferase using an ELISA, as follows: 96-well plates were coated with a recombinant luciferase protein (Promega, Madison, Wis.) by incubation of 100 µl 2 µg/ml protein in 0.1 M carbonated buffer per well. Plates were incubated overnight at 4° C., then washed three times with PBS containing 0.05% Tween 20. Wells are blocked with 200 µl PBS+1% non-fat dried milk for 1.5 h at RT and washed three times as above. Mouse sera were diluted in PBS+1% milk. 100 µl diluted sera were added to wells in duplicate and incubated 1.5 h at RT. The plates were washed three times as above. 100 µl anti-mouse polyvalent antibody conjugated to horseradish peroxidase (Sigma, St. Louis, Mo.) diluted 1:20,000 in the PBS+1% milk buffer was added to each well. The plates are washed five times as above. 100 µl tetramethylbenzidine (Sigma) was added to each well and the samples were allowed to develop. The reaction was stopped by addition of 100 µl 1.0 M $H_2SO_4$ per well and the absorbance was read at 450 nm. A standard curve was generated using a goat anti-luciferase horseradish peroxidase conjugate (Sigma).

Figure 10:
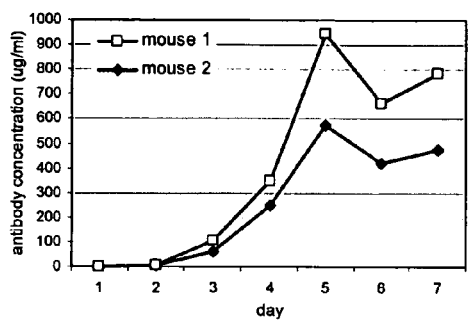
FIG. 10. IV genetic immunization: time-course of anti-luciferase antibody expression in A) mouse and B) rabbit. Animals were injected IV with an expression vector encoding the luciferase gene.
Figure 10:
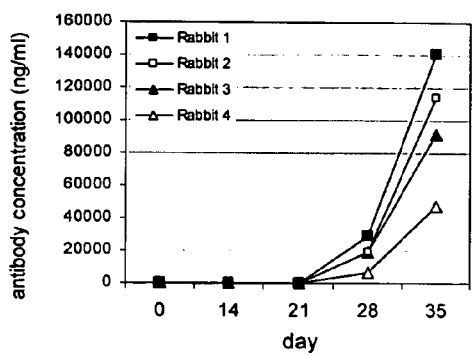

The results are shown in FIG. 10 A. The presence of anti-luciferase antibodies present in the mouse sera indicate successful induction of an immune response.

Example 16

Genetic Immunization in Rabbits

Four rabbits were injected on days 0, 14, 21 and 28 with a plasmids encoding the firefly luciferase gene under control of the cytomegalovirus promoter (pMIR48) and the ubquitin C promoter and a hepatic control region for enhancement of long-term expression (pMIR68). Two animals also received a plasmid encoding murine interleukin 2 under control of the cytomegalovirus promoter (pMIR152). For each injection, a solution containing the plasmid was inserted into the lumen of the saphenous vein as follows: A latex tourniquet was wrapped around the upper hind limb to block blood flow into and out of the leg and tightened into place with a hemostat. Injections were done into either the great or the small saphenous vein. A 23 gauge catheter was inserted, in antegrade orientation, into the lumen of the vein. A syringe pump was used to inject an efflux enhancer solution (1.0 mg papaverine in 6 ml) at a flow rate of 4-5 m/min. One to five minutes later a solution containing plasmid DNA was injected through the catheter (1 mg/kg pMIR48 or pMIR68; 2 mg/kg pMIR152 in 18-44 mls saline, 14 ml/kg animal weight.) The solution was injected in 18-30 seconds (1-2 ml/sec). The volume of solution and rate of injection were varied depending on the weight of the rabbit. The solution was injected in the direction of normal blood flow through the vein. The tourniquet was removed two minutes after the injection. Bleeding from the incision and vein puncture was controlled with pressure and a hemostatic sponge. The incision was closed with 4-0 Braun-amid suture. The procedure was completed in ~20 min.

To monitor induction of an immune reaction to luciferase in the animals, animals were bled on days—3, 14, 21, 28 and 35. The presence of antibodies in the sera, indicating induction of an immune response, was determined as above. The results are shown in FIG. 10 B. The presence of anti-luciferase antibodies present in the rabbit sera indicate successful induction of an immune response.

Example 17

Intravenous Delivery of Polynucleotides to Muscles of the Foot

This experiment was performed as in example 5 with the following differences: A tourniquet was placed just above the ankle and 100 μluciferase encoding plasmid DNA in 1 ml saline was injected in a retrograde direction at a rate of 10 ml/min into the lateral plantar vein using a 30 gauge needle catheter. No pre-injection of papaverine was performed. In two animals, the average luciferase expression in muscles of the foot was 584±58.6 ng luciferase per gram of muscle tissue. Luciferase expression was minimal in the gastrocnemius muscles (muscle proximal to the tourniquet) of the same animals.

Example 18

A Vasodilator is not Required to Intravenous Delivery of Polynucleotides to Limb Muscle Cells These experiments were performed as described in example 5 with the following differences: 250 μg pMIR48 plasmid was injected and in some animals the vasodilator papaverine was not included in the pre-injection solution. Luciferase expression was not statistically different in animals receiving papaverine compared with animals not receiving papaverine. The numbers in the table indicated the averages plus SEM for 12 limbs in 9 animals in which papaverine was used, and for 7 limbs in 7 animals in which no papaverine was injected. Four of the animals received papaverine in one hind limb and no papaverine in the other hind limb.

Example 19

Effect of Time of Vessel Occlusion Following Polynucleotide Injection

These experiments were performed as described in example 5 with the following differences: 250 μg of pMIR48 plasmid was injected and blood flow into and out of the injected leg was blocked for 0 min, 2 min, or 5 min following completion of the injection of the solution containing the polynucleotide into the vein. Blood flow was restored at the indicated time by release of the tourniquet. There was no papaverine pre-injection, and the DNA was in 4.5 ml saline solution injected in 30 sec. The results indicate that restricting blood flow for a long or shorter period following injection does not eliminate polynucleotide delivery to cells in the limb.

TABLE 12

Delivery of polynucleotides to muscles throughout rat hind limb via intravenous injection; effect of maintenance of vessel occlusion after injection.

| | ng Luciferase per gm muscle tissue | | | | | |
|---|---|---|---|---|---|---|
| treatment | quad | biceps | hamstring | gastroc | shin | total |
| 5 min (n = 3) | 88 ± 42 | 342 ± 116 | 287 ± 82 | 665 ± 407 | 115 ± 44 | 339 ± 139 |
| 2 min (n = 2) | 81 ± 24 | 182 ± 26 | 407 ± 86 | 568 ± 60 | 27 ± 4 | 274 ± 29 |
| 0 min (n = 3) | 99 ± 26 | 184 ± 32 | 210 ± 15 | 399 ± 22 | 91 ± 23 | 210 ± 17 |

Example 20

Delivery of Polynucleotides to Joint and Bone, and Bone Marrow Cells Via IV Injection ICR mice were anesthetized with 1-2% isoflurane throughout each procedure. A small latex tourniquet was wrapped tightly around the upper hind limb (above quadriceps) and held in place with a hemostat. A small incision (~1 cm) was made in the skin to expose a segment of the distal great saphenous vein. A 30 gauge needle catheter was inserted into the distal great saphenous vein, advanced about 0.5 cm and held in place during the injection. The catheter was then connected to a Harvard PHD 2000 syringe pump and the DNA (100 μg, 147 μg MCK, 280 μg Desmin) saline solution (1.0 ml) was injected (antegrade) at a rate of 8 ml/min. The plasmid DNA encoded with the luciferase gene or the β-galactosidase gene. The tourniquet was removed 2 minutes after injection and the skin was closed with 5-0 suture. One day after injection the tissue was harvested homogenized in 0.5 ml of lysis buffer and assayed for luciferase expression. The bone marrow cells were harvested by opening the femur and scraping out the bone marrow with a forceps. The remaining

TABLE 11

Delivery of polynucleotides to muscles throughout rat hind limb via intravenous injection, with or without a vasodilator pre-injection.

| | ng Luciferase per gm muscle tissue | | | | | |
|---|---|---|---|---|---|---|
| treatment | quad | biceps | hamstring | gastroc | shin | total |
| with papaverine | 363 ± 73 | 648 ± 154 | 850 ± 158 | 1748 ± 273 | 227 ± 51 | 894 ± 131 |
| without papaverine | 205 ± 31 | 796 ± 123 | 741 ± 90 | 1843 ± 336 | 451 ± 159 | 841 ± 81 | femur was assayed for bone expression. The joint tissue included the synovial lining, tendons, cartilage and connective tissue from the joint capsule.

TABLE 13

Delivery of polynucleotide to bone cells of the femur via IV injection.

| | Luciferase expression (pg luciferase/g tissue) | | |
|---|---|---|---|
| animal | MCK promoter | Desmin promoter | CMV promoter |
| #1 | 2096 | 459 | 620 |
| #2 | 3321 | 292 | 162 |
| #3 | 5428 | 201 | 175 |
| #4 | 31299 | 481 | 676 |
| #5 | 3061 | 913 | 11272 |
| #6 | 3685 | 1225 | 5601 |
| #7 | 2986 | 606 | 9860 |
| #8 | 2298 | 530 | 9801 |
| #9 | | 1542 | |
| #10 | | 471 | |
| #11 | | 344 | |
| average | 6772 | 642 | 4771 |

TABLE 14

Delivery of polynucleotides to bone marrow cells via IV injection.

| | Luciferase expression (pg luciferase/g tissue) | | |
|---|---|---|---|
| animal | MCK promoter | Desmin promoter | CMV promoter |
| #1 | 188 | 69.5 | 205 |
| #2 | 106 | 60.7 | 67.9 |
| #3 | 299 | 44.2 | 24.3 |
| #4 | 2438 | 87.6 | 52.4 |
| #5 | 249 | 13842 | 243 |
| #6 | 363 | 1664 | 745 |
| #7 | 1033 | 758 | 364 |
| #8 | 849 | 427 | 1660 |
| #9 | | 1024 | |
| #10 | | 1324 | |
| #11 | | 153 | |
| average | 691 | 1768 | 420 |

TABLE 15

Delivery of polynucleotides to cells of the joint via IV injection.

| | Luciferase expression (pg luciferase/g tissue) | | |
|---|---|---|---|
| animal | MCK promoter | Desmin promoter | CMV promoter |
| #1 | 69095 | 6407 | 6058 |
| #2 | 42744 | 31546 | 3117 |
| #3 | 52951 | 15445 | 2331 |
| #4 | 22727 | 22655 | 11669 |
| #5 | 36557 | 5442 | 142015 |
| #6 | 57619 | 3689 | 122177 |
| #7 | 15707 | 876 | 90531 |
| #8 | 21105 | 2732 | 43237 |
| #9 | | 2083 | |
| #10 | | 4062 | |
| #11 | | 8123 | |
| average | 39813 | 9369 | 52642 |

Figure 12:
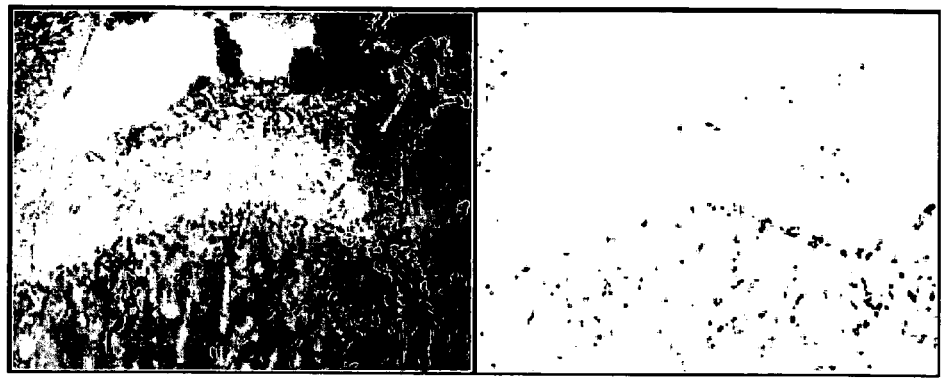
FIG. 12. Photomicrograph of LacZ staining in bone following IV delivery of the β-galactosidase transgene. The left panel shows an image of the bone and joint cross-section. The right-hand panel shows the same section stained with LacZ.

FIG. 12 shows the presence of cells in bone transfected with the β-galactosidase transgene as indicated by LacZ staining. The left panel shows an image of the bone and joint cross-section. The darker to light transition near the mid-section of the photomicrograph indicates the transition from bone and cartilage. The right-hand panel shows the same section stained with LacZ, demonstrating the presence of transfected bone cells (dark spots).

For delivery to cell of the joint in rat, the procedure was the same as example #5 except that 2 mg of DNA (CMV-luciferase) was injected. At 24 hours after injection, the rats were euthanized and the intact joint (head of the tibia, femur, patella and all joint capsule tissues) was harvested, homogenized in 5.0 ml of lysis buffer and assayed for luciferase expression.

TABLE 16

Delivery of polynucleotides to cells of the joint via IV injection.
Luciferase activity in right knee joint

| | rat 1 | rat2 | control |
|---|---|---|---|
| RLUs | 1,670,015 | 1,369,799 | 1,456 |

Example 21

Effect of Volume of Injection Solution and Rate of Injection on IV Delivery of Polynucleotides to Limb Skeletal Muscle Cells in Rat and Mouse IV injections into rat were performed as in example 5, except that the injection solution was injected at varying rates.

TABLE 17

Delivery of polynucleotides to rat limb muscle cells using various injection rates.

| | study 1 | | | | study 2 | |
|---|---|---|---|---|---|---|
| | injection rate ml/min | | | | | |
| | 12 | 6 | 3 | 1.5 | 1 | 0.6 |
| ng luciferase per g tissue | 252 ± 6 | 358 ± 28 | 206 ± 41 | 76 ± 21 | 128 ± 32 | 97 ± 8.3 |

IV injections into C57 mice were performed as in example 10, except that the injection solution volume and injection rate were varied.

TABLE 18

Delivery of polynucleotides to mouse limb muscle cells using various injection volumes and rates.

| injection volume | enzyme activity | injection rate (ml/min) | | | | | |
|---|---|---|---|---|---|---|---|
| | | 2 | 4 | 8 | 12 | 15 | 18 |
| 0.2 ml | luciferase | | | | | 113 | |
| | CPK | | | | | 416 | |
| | | | | | | n = 2 | |
| 0.4 ml | luciferase | | | | | 253 | |
| | CPK | | | | | 403 | |
| | | | | | | n = 4 | |
| 0.6 ml | luciferase | 229 | 411 | 460 | 423 | 626 | 808 |
| | CPK | 194 | 356 | 163 | 1227 | 1018 | 320 |
| | | n = 3 | n = 3 | n = 3 | n = 3 | n = 4 | n = 3 |

TABLE 18-continued

Delivery of polynucleotides to mouse limb muscle cells using various injection volumes and rates.

| injection volume | enzyme activity | injection rate (ml/min) | | | | | |
|---|---|---|---|---|---|---|---|
| | | 2 | 4 | 8 | 12 | 15 | 18 |
| 0.8 ml | luciferase | | 232 | 385 | 462 | 375 | 203 |
| | CPK | | 878 | 298 | 1600 | 1710 | 754 |
| | | | n = 2 | n = 2 | n = 1 | n = 6 | n = 3 |
| 1.0 ml | luciferase | 299 | 264 | 518 | 497 | 606 | 612 |
| | CPK | 286 | 329 | 216 | 330 | 277 | 511 |
| | | n = 2 | n = 4 | n = 6 | n = 10 | n = 9 | n = 5 |
| 1.25 ml | luciferase | 109 | 426 | 882 | | 310 | |
| | CPK | | | | | 638 | |
| | | n = 1 | n = 2 | n = 2 | | n = 4 | |
| 1.5 ml | luciferase | 154 | 549 | 1050 | 482 | 706 | 561 |
| | CPK | 319 | 522 | 573 | 279 | 515 | 237 |
| | | n = 1 | n = 2 | n = 2 | n = 2 | n = 2 | n = 1 | luciferase = ng/g tissue
CPK = U/L

Example 22

Intravenous Injection into the Saphenous Vein Provides Effective Delivery of Polynucleotides to Limb Skeletal Muscle 120-140 g adult Sprague-Dawley rats were anesthetized with 80 mg/kg ketamine and 40 mg/kg xylazine and the surgical field was shaved and prepped with an antiseptic. The animals were placed on a heating pad to prevent loss of body heat during the surgical procedure. A 4 cm long abdominal midline incision was made after which skin flaps were folded away and held with clamps to expose the target area. A moist gauze was applied to prevent excessive drying of internal organs. Intestines were moved to visualize the iliac veins and arteries. Microvessel clips was placed on the femoral vein and the epigastric vein. An efflux enhancer solution (e.g., 0.5 mg papaverine in 1.5 ml saline) was injected into the small saphenous vein though a 27 g needle. 1-10 minutes later, a 27 G butterfly needle was inserted into the same site and 7.5 ml normal saline containing 500 μg pMIR48 plasmid DNA encoding firefly Luciferase was injected at a rate of 25 ml/min. Fluid was injected in the direction of normal blood flow. The microvessel clips were removed 2 minutes after the injection and bleeding was controlled with pressure and gel foam. The abdominal muscles and skin were closed with 4-0 dexon suture. Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per gram of muscle tissue was determined. The muscle descriptions indicate the following muscle groups of the hindlimb: Quad—anterior muscles of upper leg; Biceps—medial muscles of upper leg; Hamstring—posterior muscles of upper leg; Gastroc—posterior muscles of lower leg; Shin—anterior muscles of lower leg; Foot—muscles of the dorsal foot. Luciferase expression was observed in muscles throughout the limb distal to the occlusion. Highest expression levels were observed near the site of injection. The results indicate that occlusion of as little as one or two veins is sufficient to provide for polynucleotide delivery to extravascular limb cells following intravenous injection.

TABLE 19

Luciferase expression in individual muscle groups (ng Luciferase/g Muscle)

| animal | quad | biceps | hamstring | gastroc | shin | foot | total |
|---|---|---|---|---|---|---|---|
| 1 | 206.2 | 658.1 | 565.6 | 1179.1 | 310.0 | 1.4 | 610.9 |
| 2 | 0.3 | 8.2 | 140.5 | 519.7 | 145.1 | 0.1 | 143.9 |
| 3 | 56.5 | 189.0 | 403.7 | 584.8 | 151.4 | 3.8 | 302.1 |

Example 23

Figure 11:
FIG. 11. Photomicrographs of mouse hind limb gastrocnemius muscle stained for β-galactosidase following single intravenous injection of $0.19 \times 10^9$ transducing units of adeno-associated virus in 0.8 ml saline at a rate of 3 ml per minute.
Figure 11:
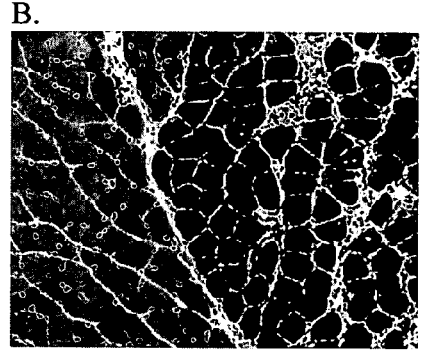

Delivery of Adeno-Associated Virus (AAV) to Limb Muscle Cells Via Increased Pressure IV Injection Mice were anesthetized with 1-2% isoflurane throughout each procedure. A small latex tourniquet was wrapped tightly around the upper hind limb (above quadriceps) and held in place with a hemostat. A small incision (~1 cm) was made in the skin to expose a segment of the distal great saphenous vein. A 30 gauge needle catheter was inserted into the distal great saphenous vein, advanced about 0.5 cm and held in place during the injection. The catheter was connected to a Harvard PHD 2000 syringe pump and the AAV ($0.19 \times 10^9$ transducing units, CMV-LacZ) saline solution (0.8 ml) injected (antegrade) at a rate of 3 ml/min. The tourniquet was removed 2 minutes after injection and the skin was closed with 5-0 suture. Two weeks after injection, the limb muscles were harvested and frozen in cold isopentane and stored at −80° C. 10 μm thick cryosections were made and fixed in 1.25% gluteraldehyde. The sections were then incubated in X-gal staining solution (Mirus Corporation) for 1 hour at 37° C. FIG. 11 shows photomicrographs of mouse hind limb gastrocnemius muscle stained for β-galactosidase, showing that AAV was efficiently delivered to muscle cells.

Example 24

IV Delivery of Macromolecules to Extravascular Limb Cells

Figure 13:
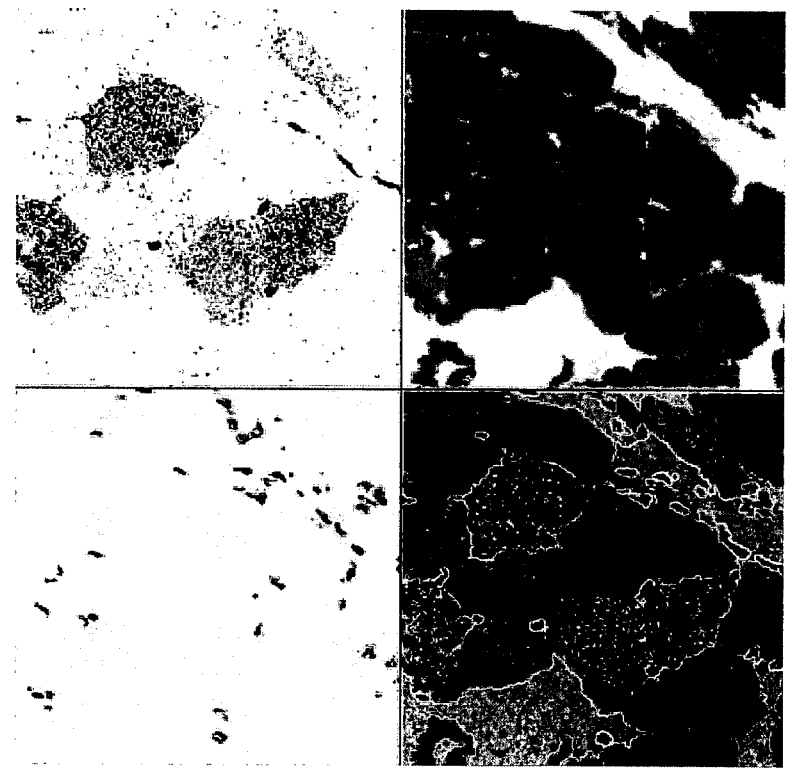
FIG. 13. Photomograph of mouse limb skeletal muscle after IV injection of rhodamine-labeled 70 kDa dextran into the saphenous vein distal to an applied tourniquet. The upper left-hand panel shows the rhodamine-labeled dextran. The upper right-hand panel show the location of muscle cells. The lower left-had paned shows the location of nuclei. The lower right-hand panel show the composite picture.

This study was done in mice. ICR mice prepped and injected as described in example 20 except that 100 μg rhodamine-labeled 70 kDa dextran polymer in saline was injected. Muscle tissue was harvested 1 hour after injection prepped for fluorescent microscopy. As shown in FIG. 13, the labeled dextran was effectively delivered to skeletal muscle cells in the limb. The upper left-hand panel shows the rhodamine-labeled dextran. The upper right-hand panel show the location of muscle cells. The lower left-had paned shows the location of nuclei. The lower right-hand panel show the composite picture.

Example 25

Delivery of Polynucleotides to Mouse Limb Cells, Expression Cassette Comparison

ICR mice were anesthetized with 1-2% isoflurane throughout each procedure. A small latex tourniquet was wrapped tightly around the upper hind limb (above quadriceps) and held in place with a hemostat. A small incision (~1 cm) was made in the skin to expose a segment of the distal great saphenous vein. A 30 gauge needle catheter was inserted into the distal great saphenous vein, advanced about 0.5 cm and held in place during the injection. The catheter was then connected to a Harvard PHD 2000 syringe pump and the 50 µg DNA in 1.0 ml saline solution was injected (antegrade) at a rate of 8 ml/min. The plasmid DNA encoded with the luciferase gene or the β-galactosidase gene. The tourniquet was removed 2 minutes after injection and the skin was closed with 5-0 suture. Two or seven days after injection the limb muscle tissue was harvested, homogenized in 0.5 ml of lysis buffer and assayed for luciferase expression. Four different expression cassettes, with different promoters, were delivered: pMIR048 containing the CMV promoter, pMIR057 containing the MCK promoter in a Kan resistance backbone, pMCK-Luc containing the MCK promoter in an Amp resistance backbone, and pMIR068 containing the HCR-Ub promoter. For each time point and with each vector, 4-5 mice were assayed.

TABLE 20

Luciferase expression in skeletal muscle cells from different expression cassettes following IV delivery of plasmid DNA to the skeletal muscle cells

| plasmid | ng luciferase per gram muscle tissue | |
|---|---|---|
| | day 2 | day 7 |
| pMIR048 | 868 ± 273 | 2910 ± 1510 |
| pMIR057 | 11.3 ± 5.06 | 611 ± 324 |
| pMIR068 | 91.7 ± 23.1 | 517 ± 73.3 |
| pMCK-Luc | 15.2 ± 3.93 | 1030 ± 263 |

Example 26

Delivery of Luciferase DNA Vector to Rat Limb Muscle Cells Via Venous Injection

500 µg of pDNA (pCI-Luc-K) in normal saline solution (NSS) was used for all intravenous injections into ~150 g Sprague-Dawley rats. Blood flow to and from the limb was restricted just prior to and during the injection, and for 2 min post-injection by placing a tourniquet around the upper leg Oust proximal to/or partially over the quadriceps muscle group). In some rats, 1.5 ml of a papaverine solution was injected (250 µg papaverine in 1.5 ml NSS) at a distal site in the great saphenous vein. In rats receiving papaverine pre-injection, 1 or 5 min later pDNA was injected into the great saphenous vein of the distal hind limb at a rate of 3 ml per ~20 seconds (10 ml/min; FIG. 1). In rats not receiving papaverine injection, pDNA in 4.5 ml saline (same total volume injected) was injected in 30 sec. The intravenous injections were performed in an anterograde direction (i.e., with the blood flow) via a needle catheter connected to a programmable Harvard PHD 2000 syringe pump (Harvard Instruments). Rats were euthanized at 5 days post-injection and limb muscles were harvested and separated into 6 groups (quadriceps, biceps, hamstring, gastrocnemius, shin and foot). The luciferase activity from each muscle group was determined as previously described (Zhang et al. 2001) and total level of luciferase expression per gram of muscle tissue was determined. 3 rats were injected for each condition. The results indicate that polynucleotides are effectively delivered to limb skeletal muscle cells, as evidenced by luciferase expression, both with and without pre-injection of a vasodilator.

TABLE 21

Delivery of nucleic acid to limb muscle cells with and without vasodilator pre-injection.

| pre-injection | ng luciferase per gram muscle tissue | | | | | |
|---|---|---|---|---|---|---|
| | quad | biceps | hamstring | gastroc | shin | total |
| 5 min | 99 ± 46 | 397 ± 188 | 248 ± 41 | 626 ± 363 | 122 ± 84 | 300 ± 87 |
| 1 min | 147 ± 107 | 309 ± 99 | 206 ± 36 | 398 ± 116 | 93 ± 61 | 242 ± 51 |
| none | 106 ± 37 | 328 ± 43 | 406 ± 91 | 874 ± 312 | 120 ± 17 | 387 ± 62 |

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivery of polynucleotides to extravascular cells in a mammalian limb comprising;
    a) supplying said polynucleotides in a volume of pharmaceutically acceptable solution of about 0.2 to about 0.6 milliliters of said solution per milliliter of displaced target area volume,
    b) inserting an injection devise into a vein in said limb;
    c) forming an occlusion of said vein proximal to an intended site of injection of said polynucleotides; and,
    d) injecting said solution into said vein in an antegrade direction wherein the volume and rate of injection combine to increase permeability of veins and venules in said limb and increase the volume of extravascular fluid in said target area thereby delivering said polynucleotides to said extravascular cells in said limb distal to said occlusion.

2. The process of claim 1 wherein said vein consists of a superficial vein.

3. The process of claim 1 wherein said vein consists of a deep vein.

4. The process of claim 1 wherein forming an occlusion comprises applying a device for impeding blood flow to the surface of the skin of said limb and applying sufficient pressure against said limb with said device to impede blood flow to and from said limb.

5. The process of claim 4 wherein said device for impeding blood flow is selected from the group consisting of: tourniquet, double tourniquet, double cuff tourniquet, cuff, sphygmomanometer, oscillotonometer, oscillometer, and haemotonometer.

6. The process of claim 1 wherein said injector is selected from the group consisting of: catheter, syringe needle, cannula, stylet, balloon catheter, multiple balloon catheter, single lumen catheter, and multilumen catheter.

7. The process of claim 1 wherein said extravascular cell is selected from the group consisting of: skeletal muscle cell, joint cell, cartilage cell, connective tissue cell, mesenchyme cell, mast cells, macrophages, histiocyte, tendon cell, bone cell, bone marrow cell, skin cell, lymph node cell and stroma cell.

8. The process of claim 1 wherein said polynucleotide consists of a naked polynucleotide.

9. The process of claim 1 wherein said polynucleotides are comprised in viral vectors.

10. The process of claim 9 wherein the viral vectors consist of adenoassociated viruses.

11. The process of claim 9 wherein the viral vectors consist of adenoviruses.

12. The process of claim 1 wherein said polynucleotides are associated in complexes with transfection agents.

13. The process of claim 1 wherein said polynucleotides each comprise an expressible gene.

14. The process of claim 13 where said gene encodes a polypeptide selected from the list consisting of: secreted protein, endocrine factor, non-secreted protein, antigen, and therapeutic polypeptide.

15. The process of claim 1 wherein said polynucleotides alter the expression of a gene in said cells.

16. The process of claim 1 wherein said polynucleotides are selected from the group consisting of: siRNA, antisense polynucleotide, ribozyme, RNAi inducing polynucleotide, and gene encoding an siRNA or antisense polynucleotide.

17. The process of claim 15 wherein said polynucleotides alter mRNA splicing.

18. The process of claim 15 wherein said polynucleotides alter mRNA levels.

19. The process of claim 1 further comprising injecting into a vessel in said limb one or more compounds to increase vessel permeability.

20. The process of claim 1 further comprising administering to said mammal one or more compounds selected from the list consisting of anesthetic and analgesic.

21. The process of claim 1 wherein said mammal has a disease.

22. The process of claim 21 wherein said disease is selected from the list consisting of:
metabolic disease, muscular disease, muscle injury, muscle atrophy, cancer, infectious disease, vascular disease, circulatory disorder, endocrine disorder, immune disorder.

23. The process of claim 1 wherein said mammal is at risk of having a disease.

24. A process for delivering molecules to extravascular cells in a mammalian limb comprising;
a) supplying said molecules in a volume of pharmaceutically acceptable solution of about 0.2 to about 0.6 milliliters of said solution per milliliter of displaced target area volume,
b) inserting an injection device into a vein in said limb;
c) forming an occlusion of said vein proximal to an intended site of injection of said polynucleotide; and,
d) injecting said solution into said vein in an antegrade direction wherein the volume and rate of injection combine to increase permeability of veins and venules in said limb and increase the volume of extravascular fluid in said target area thereby delivering said molecules to said extravascular cells in said limb distal to said occlusion.

25. The process of claim 24 wherein said molecules comprise a biologically active compound.

26. A process for delivering siRNA polynucleotides or siRNA-expressing polynucleotides to extravascular cells in a primate limb comprising:
a) supplying said polynucleotides in a volume of pharmaceutically acceptable solution of about 0.2 to about 0.6 milliliters of said solution per milliliter of displaced target area volume,
b) inserting an injection devise into a vein;
c) forming an occlusion of said vein proximal to an intended site of injection of said polynucleotides; and,
d) rapidly injecting said solution into said vein in an antegrade direction wherein the volume and rate of injection combine to increase permeability of veins and venules in said limb and increase the volume of extravascular fluid in said target area thereby delivering said polynucleotides to said extravascular cells in said limb distal to said occlusion.

27. The process of claim 1 wherein the rate of injection is 3-10 ml/min for injection into a saphenous vein in a mouse hindlimb.

28. The process of claim 1 wherein the rate of injection is 6-35 ml/min for injection into a saphenous vein in a rat hindlimb.

29. The process of claim 1 wherein the rate of injection is 60-120 ml/min for injection into a saphenous vein in a rabbit hindlimb.

30. The process of claim 1 wherein the rate of injection is 102-120 ml/min for injection into a limb vein in a rhesus monkey limb.

* * * * *